(12) United States Patent
Daly

(10) Patent No.: US 7,939,659 B2
(45) Date of Patent: May 10, 2011

(54) BIOLOGICAL BUFFERS WITH WIDE BUFFERING RANGES

(76) Inventor: Thomas Daly, Arlington Heights, IL (US)

(*) Notice: Subject to any disclaimer, the term of this patent is extended or adjusted under 35 U.S.C. 154(b) by 0 days.

(21) Appl. No.: 12/606,762

(22) Filed: Oct. 27, 2009

(65) Prior Publication Data

US 2010/0099868 A1   Apr. 22, 2010

Related U.S. Application Data

(63) Continuation-in-part of application No. 12/437,749, filed on May 8, 2009, now Pat. No. 7,851,652, which is a continuation-in-part of application No. 12/151,899, filed on May 9, 2008, now Pat. No. 7,635,791.

(60) Provisional application No. 61/249,090, filed on Oct. 6, 2009, provisional application No. 61/124,586, filed on Apr. 17, 2008, provisional application No. 61/135,058, filed on Jul. 16, 2009.

(51) Int. Cl.
*C07D 295/15* (2006.01)
*C07C 229/24* (2006.01)

(52) U.S. Cl. ........................ 544/171; 562/571

(58) Field of Classification Search .............. None
See application file for complete search history.

(56) References Cited

U.S. PATENT DOCUMENTS

| | | | |
|---|---|---|---|
| 3,562,273 | A | 2/1971 | Salat et al. |
| 4,112,050 | A | 9/1978 | Sartori et al. |
| 4,277,244 | A | 7/1981 | Bugaut et al. |
| 4,328,143 | A | 5/1982 | Izumi et al. |
| 4,719,049 | A | 1/1988 | Bair |
| 4,910,303 | A | 3/1990 | Su et al. |
| 5,051,212 | A | 9/1991 | Culshaw et al. |
| 5,350,837 | A | 9/1994 | Bridger et al. |
| 6,251,908 | B1 | 6/2001 | Bottcher et al. |
| 6,326,187 | B1 | 12/2001 | Jones et al. |

OTHER PUBLICATIONS

Database CAPLUS on STN, Acc. No. 1956:88978, Hardegger et al., Helvetica Chimica Acta (1956), 39, p. 980-983 (abstract).*
Database CAPLUS on STN, Acc. No. 1945:28500, Cook et al., Journal of the Chemical Society (1945), p. 399-402 (abstract).
Database CAPLUS on STN, Acc. No. 1970:473647, Acta Biologica et Medica Germanica (1970), 24(1-2), p. 189-200 (abstract).
Database CAPLUS on STN, Acc. No. 1994:49593, EP 569132 (Nov. 10, 1993) (abstract).
Database CAPLUS on STN, Acc. No 1981:463826, DE 3040729 (May 14, 1981) (abstract).
Database CAPLUS on STN, Acc. No. 1970:495314, Science (1970), 169(3940), p. 97-98 (abstract).
Norman E. Good, "Uncoupling of the Hill Reaction from Photoposphorylation by Anions", Archives of Biochem & BioPhys 96, 653-661, (1962).
Norman E. Good et al., "Hydrogen Ion Buffers for Biological Research", Biochemistry 5(2) 467-477 (1966).
Angus Chemical Co. Technical Bulletin IB 69: Tris(Hydroxymethyl)Aminomethane (Tris Amino Reg™) Cas 77-86-1 (2000).
Angus Chemical Co. Technical Bulletin IDS 10: Primary Amino Alcohols. (2000).
Angus Chemical Co. Technical Bulletin IDS 15: Nitro Alcohols. (2000).
International Search Report and Written Opinion PCT/US09/43291, Jul. 31, 2009.
Database CAPLUS on STN, Acc No. 1945:28452, J. Org Chem (1945), 10, p. 243-254 (abstract).
Database CAPLUS on STN, Acc No. 1977:96787, Bulletin de la Societe Chimique de France (1975) 5-6, Pt. 2, p. 1155-1159 (abstract).
Database CAPLUS on STN, Acc No. 1952:14360, J. Am. Chem. Soc. (1951), 73, p. 2595-2596 (abstract).
Database CAPLUS on STN, Acc. No. 1989:597338, EP 317542(May 24, 1989)(abstract).

* cited by examiner

*Primary Examiner* — Brian J Davis
(74) *Attorney, Agent, or Firm* — Clifford Kraft

(57) ABSTRACT

Amines and amine derivatives that improve the buffering range, and/or reduce the chelation and other negative interactions of the buffer and the system to be buffered. The reaction of amines or polyamines with various molecules to form polyamines with differing pKa's will extend the buffering range, derivatives that result in polyamines that have the same pKa yields a greater buffering capacity. Derivatives that result in zwitterionic buffers improve yield by allowing a greater range of stability.

7 Claims, 48 Drawing Sheets

BIOLOGICAL BUFFERS WITH WIDE BUFFERING RANGES

This is a continuation-in-part of application Ser. No. 12/437,749 filed May 8, 2009, now U.S. Pat. No. 7,851,652, which was a continuation-in-part of application Ser. No. 12/151,899 filed May 9, 2008, now U.S. Pat. No. 7,635,791, which claimed priority to U.S. Provisional application No. 61/124,586 filed Apr. 17, 2008. The present application also claims priority from U.S. Provisional application No. 61/135,058 filed Jul. 16, 2009 and U.S. Provisional application No. 61/249,090 filed Oct. 6, 2009. Applications Ser. Nos. 12/437,749, 12/151,899, 61/124,586, 61/135,058 and 61/249,090 are hereby incorporated by reference.

BACKGROUND

1. Field of the Invention

The present invention relates generally to the field of amines and more particularly to a classes of amines used as buffers in biological systems.

2. Description of the Problem Solved by the Invention

Amines are very useful compounds in the buffering of biological systems. Each class of amine has various limitations which require choosing an amine based on multiple factors to select the best amine. For example, pH buffering range is typically most important, but issues of chelation, and pH range stability, and solubility also come into play. Typically, a suboptimal buffer will result in yields that are well below the potential yield. The invention disclosed improves the yields in fermentation and purification, and improves shelf stability of proteins and amino acids.

SUMMARY OF THE INVENTION

The present invention relates to amines and amine derivatives that improve the buffering range, and/or reduce the chelation and other negative interactions of the buffer and the system to be buffered. The reaction of amines or polyamines with various molecules to form polyamines with differing pKa's will extend the buffering range, derivatives that result in polyamines that have the same pKa yields a greater buffering capacity. Derivatives that result in zwitterionic buffers improve yield by allowing a greater range of stability.

DESCRIPTION OF THE FIGURES

Attention is now directed to the following figures that describe embodiments of the present invention:

FIG. 9 shows alkoxylation of aminomethylpropanol.

FIG. 12 shows the synthesis of a series of buffers with 1-nitropropane as a starting material where n and m are integers where m+n is greater than zero and n is greater than or equal to m.

Several drawings and illustrations have been presented to aid in understanding the invention. The scope of the present invention is not limited to what is shown in the figures.

DETAILED DESCRIPTION OF THE INVENTION

Combining amines with monochloroacetic acid (MCA) or sodium vinyl sulfonate (SVS) results in products are zwitterionic buffers that can buffer in both acidic and basic pH conditions. A limited number amines are currently used for this purpose, such as, tromethamine and ammonia. The reaction of amines, alcohols, and aminoalcohols with acrylonitrile (via the Michaels Addition), followed by reduction results in amines and polyamines that have a broad buffering range. The further derivatization of the amines and polyamines with MCA and SVS yields a further crop of amine buffers with desirable properties. One skilled in the art will recognize that MCA and sodium monochloroacetic acid (SMCA) can be used interchangeably.

The reaction of tromethamine as described above yields the products in FIG. 1. In step 1 in FIG. 1 where the acrylonitrile is added to the amine a branched structure wherein the addition of acrylonitrile results in a tertiary amine is shown. In reality, particularly when n is greater than 1, a mixture of products is obtained that is both tertiary and secondary. For the invention disclosed herein, n may equal any integer greater than zero, including 1. Controlling the reaction temperature, pressure and agitation will allow the mixture to be predominately secondary (such as when m=n) or tertiary amine, m can be any integer less than or equal n. Furthermore, this selection can take place in adding acrylonitrile to the amine that results, allowing a progressively more branched product. It is within the scope of the invention disclosed herein to include these additional types of products and their subsequent derivatives described herein.

Figure 1:
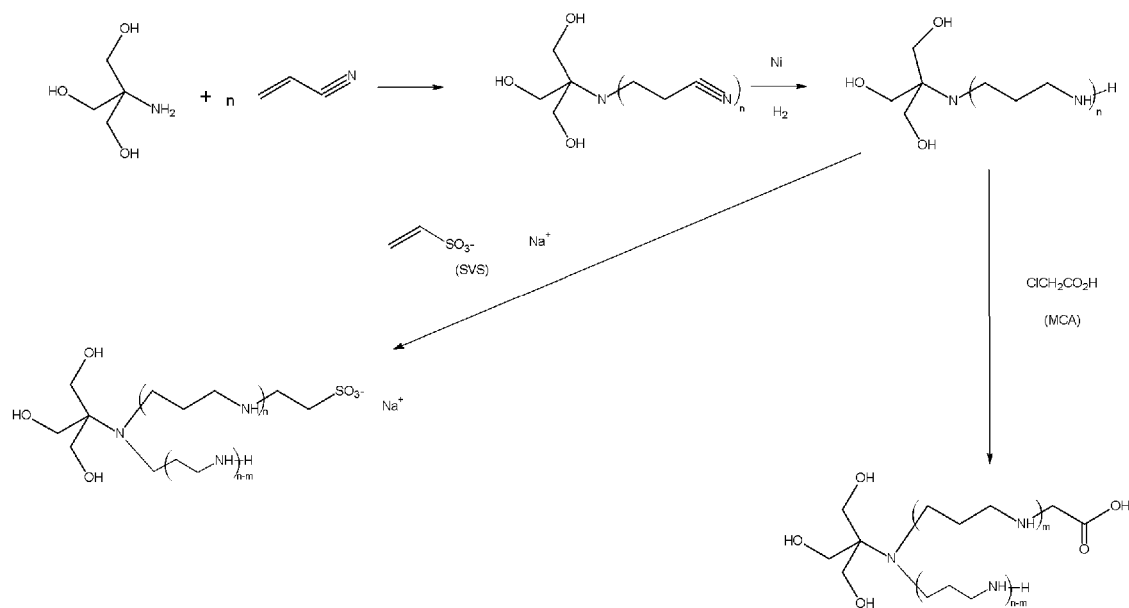
FIG. 1 shows the derivation of polyamines and zwitterionic buffers from tromethamine.

With regard to the reaction of the polyamine resulting from the second step in FIG. 1. FIG. 1 shows the addition of only one mole of SVS or MCA, it is known in the art, that a second mole may be added to obtain a product with a second zwitterionic group. Furthermore, in the case where the product has repeated additions of acrylonitrile and reduction to the amines, the branched products may have many more zwitterionic groups. Also, it is to be noted that, while the sulfonates are shown as sodium salts, other salts and the free acids (non-salted form) are also within the scope of this invention.

Other amines that would make excellent starting materials in place of tromethamine are 2-amino-2-methyl-1-propanol, 2-amino-1-butanol, 2-amino-2-ethyl-1,3-propanediol, 2-amino-2-methyl-1,3-propanediol, and dihydroxymethylaminomethane.

Additionally, fatty amines, such as lauryl amine, coco amine, tallow amine, and oleoyl amine, and fatty ether amines, such as bis-(2-hydroxyethyl) isodecyloxypropylamine, when reacted with SVS produce mild surfactants that find utility where zwitterionic surfactants are desired, including personal care.

Figure 2:
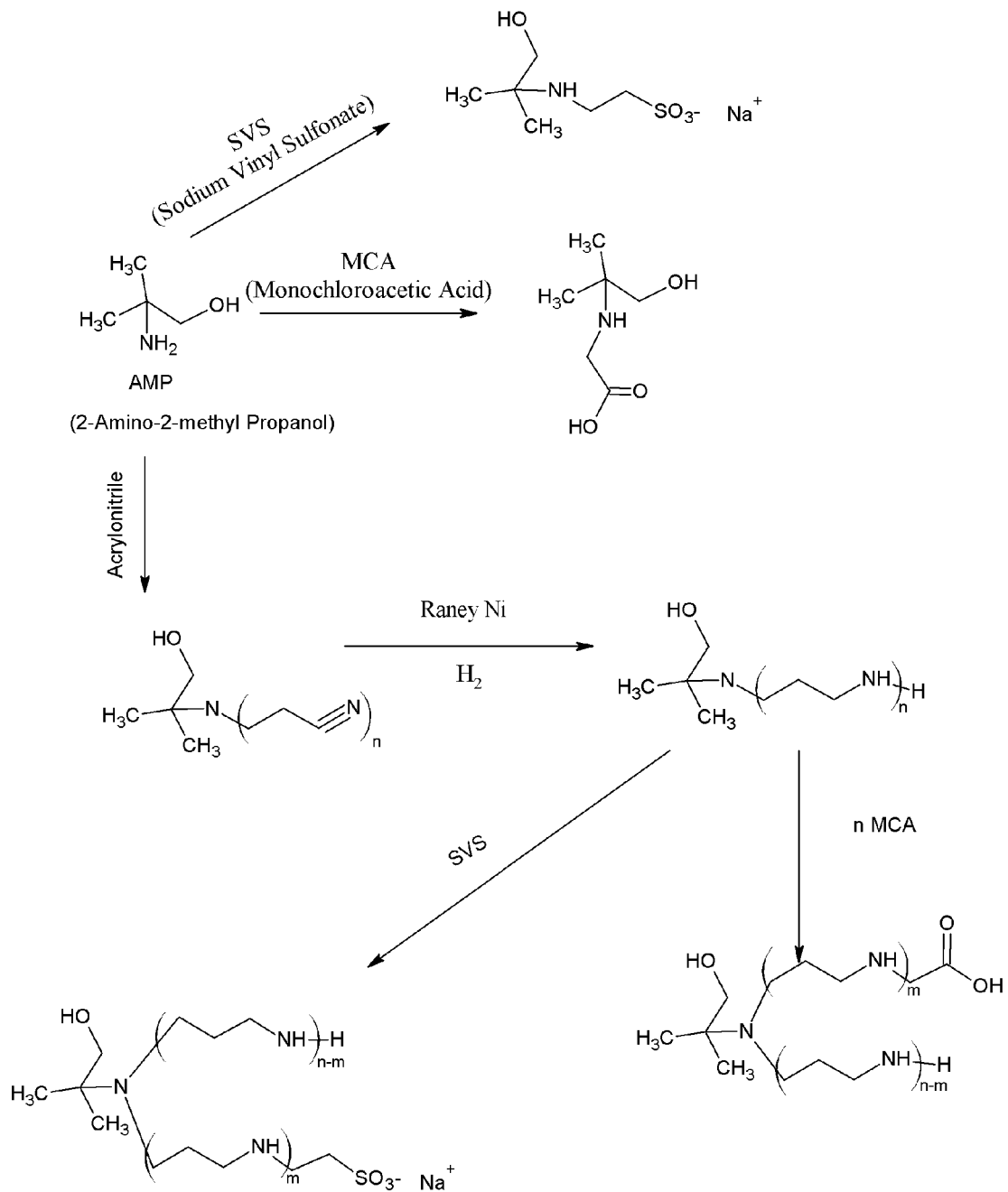
FIG. 2 shows the derivation of zwitterionic buffers and polyamines from aminomethylpropanol.

Other amines that are shown in FIG. 2 are produced via a similar series of reactions, except that FIG. 2 includes zwitterionic buffers from the amine 2-amino-2-methyl-1-propanol, as well as the polyamines derived from the reaction with acrylonitrile and the subsequent derivatives described above. Other amines can be utilized in addition to 2-amino-2-methyl-1-propanol to obtain excellent buffers are 2-amino-1-butanol, 2-amino-2-ethyl-1,3-propanediol, 2-amino-2-methyl-1,3-propanediol, and dihydroxymethylaminomethane. Reaction conditions could be created such that the alcohol groups on the amines listed above could be reacted with acrylonitrile as well, and then reduced to the amines and, if desired, reacted with SVS or MCA to impart zwitterionic character.

Polyamines with good properties for use in biological fermentations, purifications, storage and general handling can also be produced through the reaction of nitroalcohols and acrylonitrile, followed by reduction. Additional derivatization with SVS or MCA will result in zwitterionic buffers with a very large buffering range and capacity.

Figure 3:
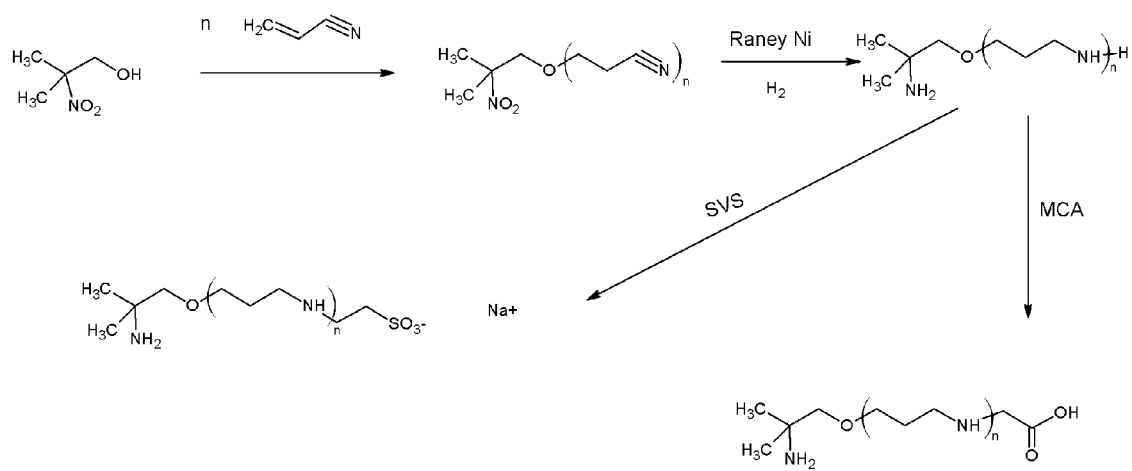
FIG. 3 shows the reaction of 2-methyl-2-nitro-1-propanol with acrylonitrile and its derivatives.

FIG. 3 shows the reaction of 2-methyl-2-nitro-1-propanol with acrylonitrile and its derivatives.

Figure 4:
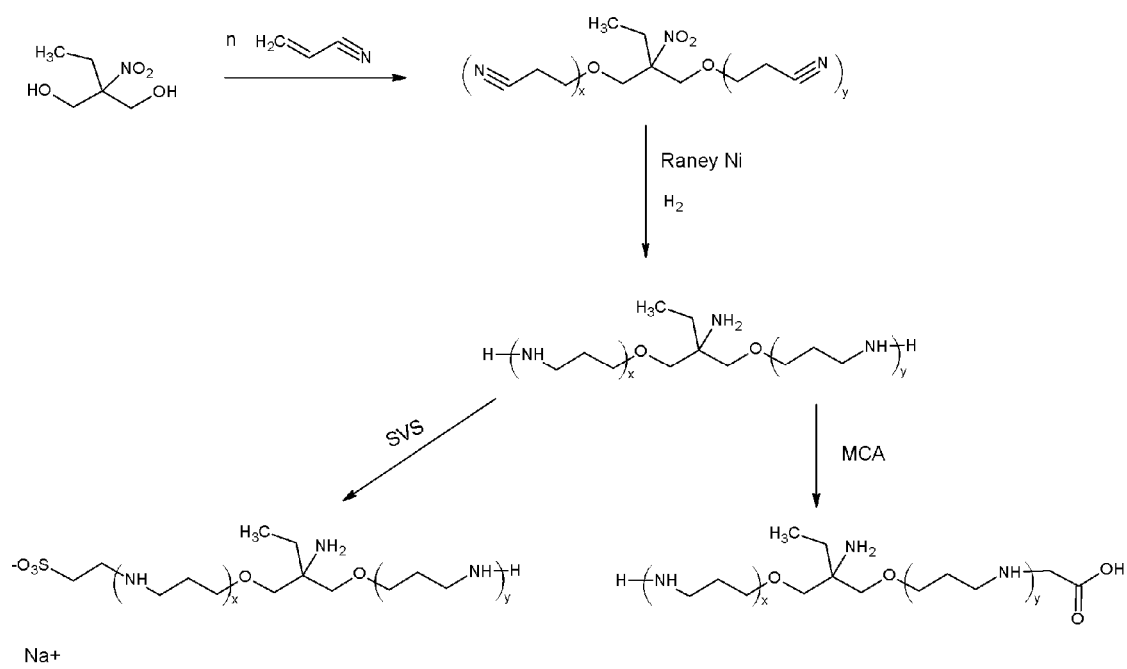
FIG. 4 shows the reaction of 2-nitro-2-ethyl-1,3-propanediol with acrylonitrile and its derivatives where x,y,and n are all integers where x and y are chosen independently, such that x+y=n and n is greater than zero.

FIG. 4 shows the reaction of 2-nitro-2-ethyl-1,3-propanediol with acrylonitrile and its derivatives where x,y,and n are all integers where x and y are chosen independently, such that $x+y=n$ and n is greater than zero.

Figure 5:
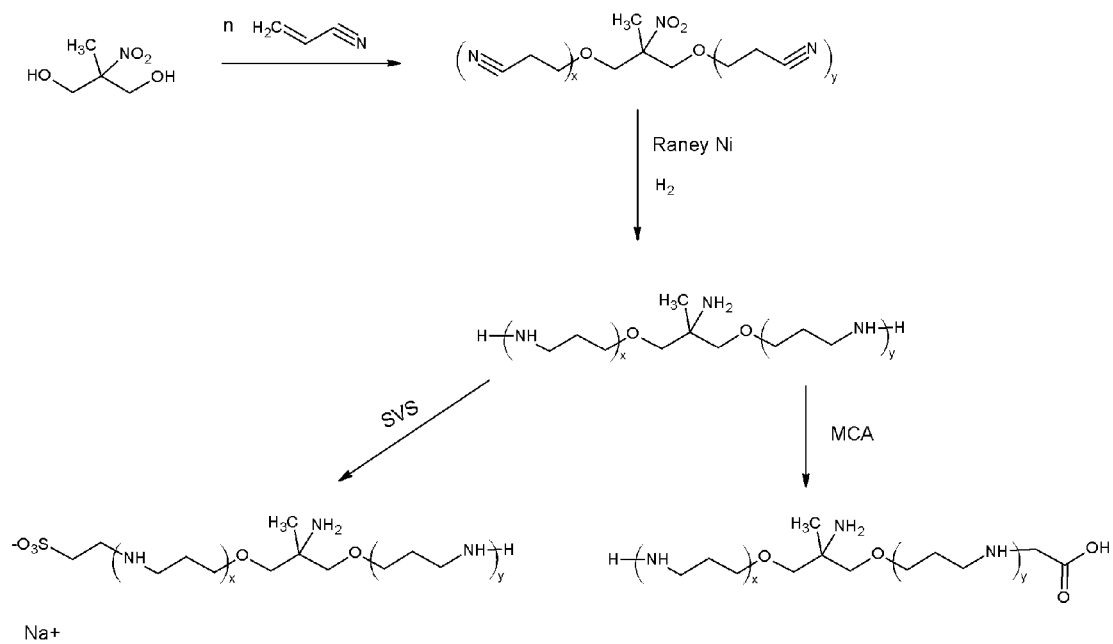
FIG. 5 shows the reaction of 2-nitro-2-methyl-1,3-propanediol with acrylonitrile and its derivatives where x,y,and n are all integers where x and y are chosen independently, such that x+y=n and n is greater than zero.

FIG. 5 shows the reaction of 2-nitro-2-methyl-1,3-propanediol with acrylonitrile and its derivatives where x,y,and n are all integers where x and y are chosen independently, such that $x+y=n$ and n is greater than zero.

Figure 6:
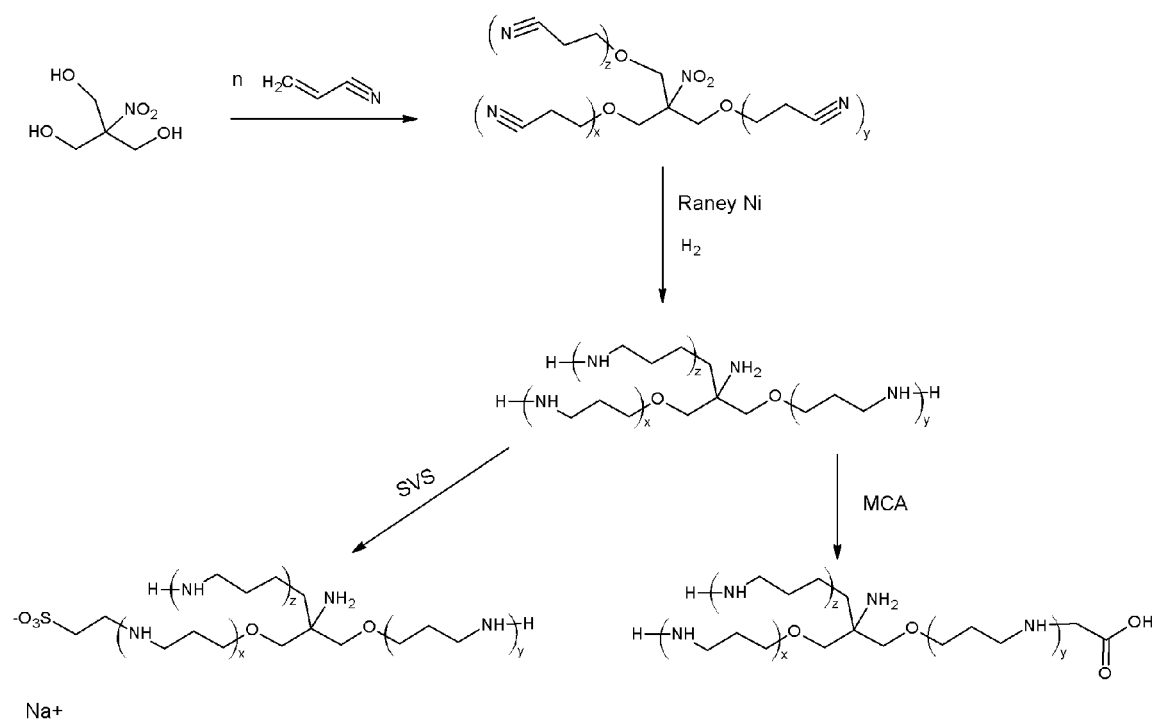
FIG. 6 shows the reaction of tris(hydroxymethyl)nitromethane with acrylonitrile and its derivatives where x,y, z, and n are all integers where x, y and z are chosen independently, such that x+y+z=n and n is greater than zero.

FIG. 6 shows the reaction of tris(hydroxymethyl)nitromethane with acrylonitrile and its derivatives where x,y, z, and n are all integers where x, y and z are chosen independently, such that $x+y+z=n$ and n is greater than zero.

Figure 7:
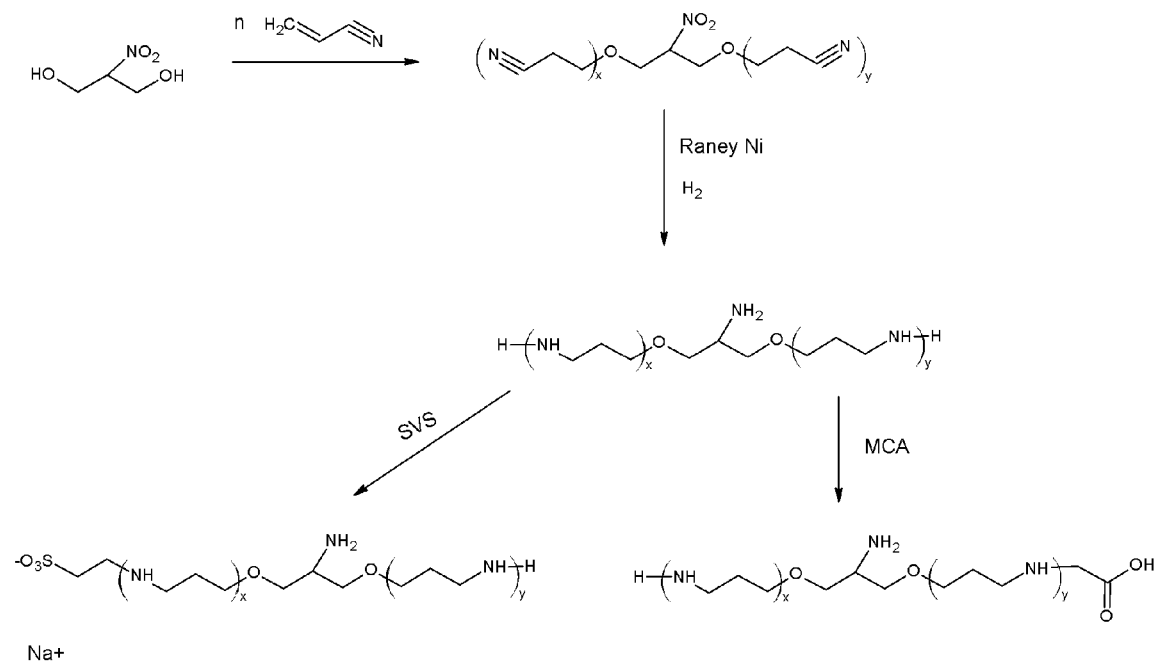
FIG. 7 shows the reaction of 2-nitro-1,3-propanediol with acrylonitrile and its derivatives where x,y,and n are all integers where x and y are chosen independently, such that x+y=n and n is greater than zero.

FIG. 7 shows the reaction of 2-nitro-1,3-propanediol with acrylonitrile and its derivatives where x,y,and n are all integers where x and y are chosen independently, such that $x+y=n$ and n is greater than zero.

Figure 8:
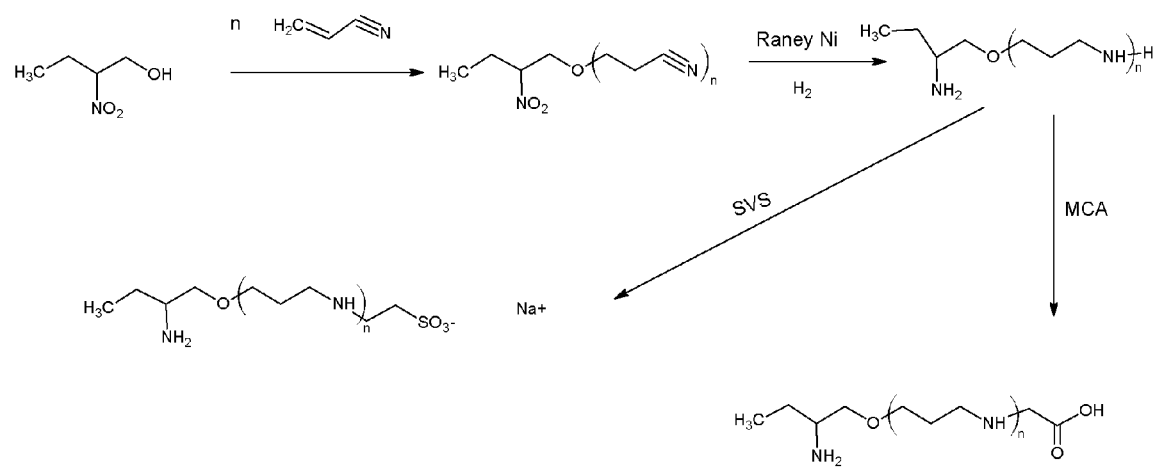
FIG. 8 shows the reaction of 2-nitro-1-butanol with acrylonitrile and its derivatives.

FIG. 8 shows the reaction of 2-nitro-1-butanol with acrylonitrile and its derivatives.

FIGS. 2 through 8 are subject to the same clarifications as FIG. 1 with regard to the cyanoethylation and the formation of a more linear or branched structure as well as the addition of SVS or MCA in molar equivalents of primary amine groups or less than molar equivalents of primary amine groups present.

Figure 9:
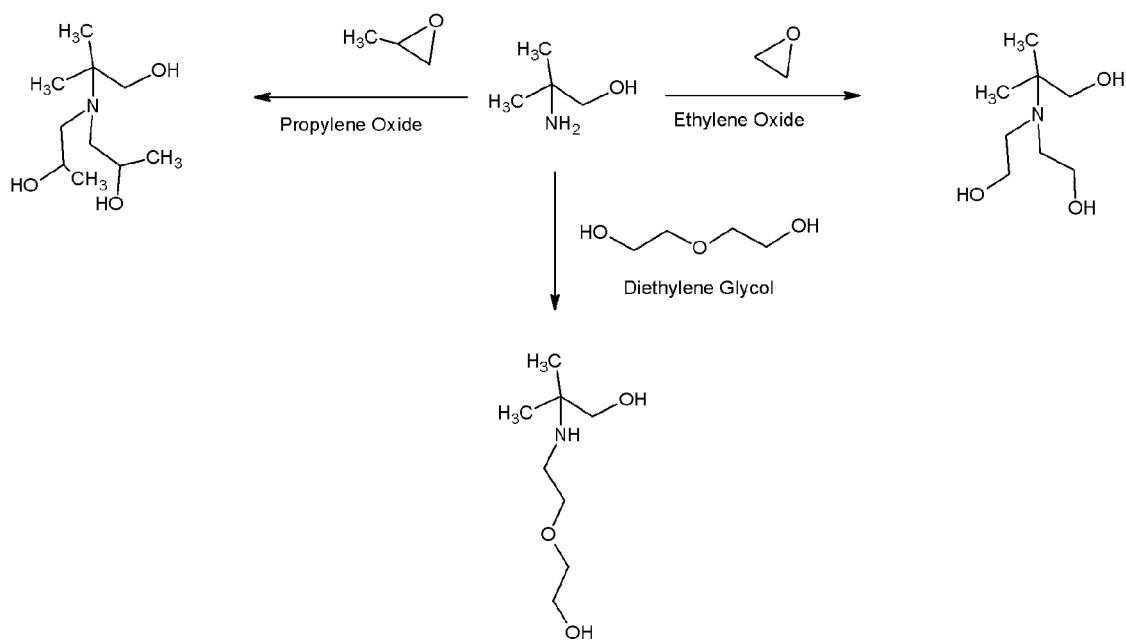
FIG. 9 shows

The buffers described thus far may also be ethoxylated, propoxylated, or butoxylated to modify their properties. Ethoxylation will tend to impart surfactancy to the resulting product. Propoxylation will add surfactancy, but also reduce the water solubility. This is useful in emulsion breaking and reverse emulsion breaking, this will also find utility in breaking up and dissolving biofilms. This is also desired in oil-field applications. Butoxylation will similarly shift the HLB to the hydrophobic. Combinations of ethoxylation, propoxylation, and butoxylation can be tailored to specific emulsion and reverse emulsion forming and breaking requirements. FIG. 9 shows alkoxylation of aminomethylpropanol. The direct 2 mole ethoxylation of 2-amino-2-methyl-1-propanol with 2 moles of ethylene oxide, as shown in FIG. 9 produces an excellent biological buffer with less chelation than 2-amino-2-methyl-1-propanol. The reaction of 2-amino-2-methyl-1-propanol with propylene oxide or butylene oxide yields a similarly less chelating product, as does the reaction with diethylene glycol. The reaction product of 2-amino-2-methyl-1-propanol with 1 mole of diethylene glycol as shown in FIG. 9 produces an ideal amine for gas scrubbing of $H_2S$. This product is particularly useful because it does not bind to carbon dioxide and carbon monoxide in any appreciable amount. Thus making it ideal for tail gas scrubbing and maximizing the capacity of sulfur plants in refineries. Similar performance is seen with the reaction of the following amines 2-amino-1-butanol, 2-amino-2-methyl-1,3-propanediol, 2-amino-2-ethyl-1,3-propanediol, tris(hydroxylmethyl)aminomethane, and 2-amino-1,3-propanediol.

Figure 10A:
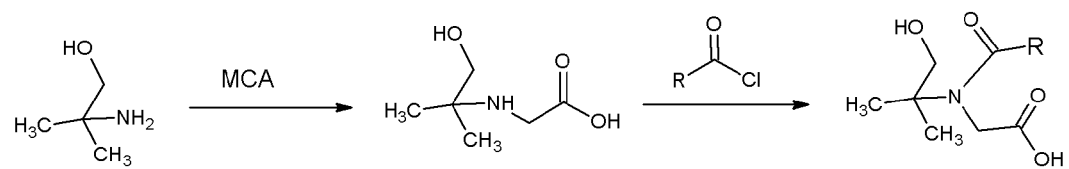
FIG. 10A shows the synthesis of a very mild, high foaming, surfactant derived from MCA.
Figure 10B:
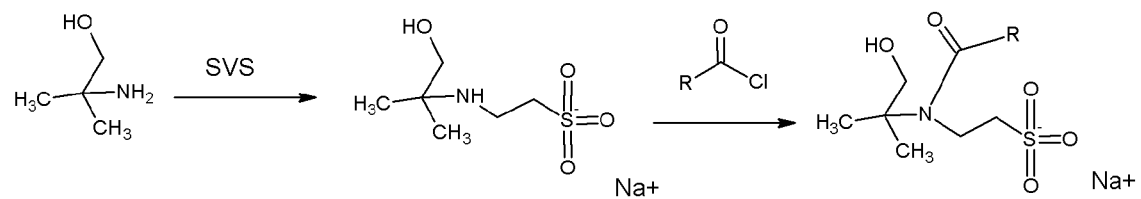
FIG. 10B shows the synthesis of a very mild, high foaming, surfactant derived from SVS.

The buffers described herein also make excellent starting materials for surfactants. FIG. 10A shows the synthesis of 2 very mild, high foaming, surfactants that are well suited for personal care applications were irritation is problematic, such as baby shampoo and face cleansers. Similar results are seen in FIG. 10B when 2-amino-1-butanol, 2-amino-2-methyl-1,3-propanediol, 2-amino-2-ethyl-1,3-propanediol, tris(hydroxylmethyl)aminomethane, and 2-amino-1,3-propanediol are used as the starting material in place of 2-amino-2-methyl-1-propanol.

Figure 11:
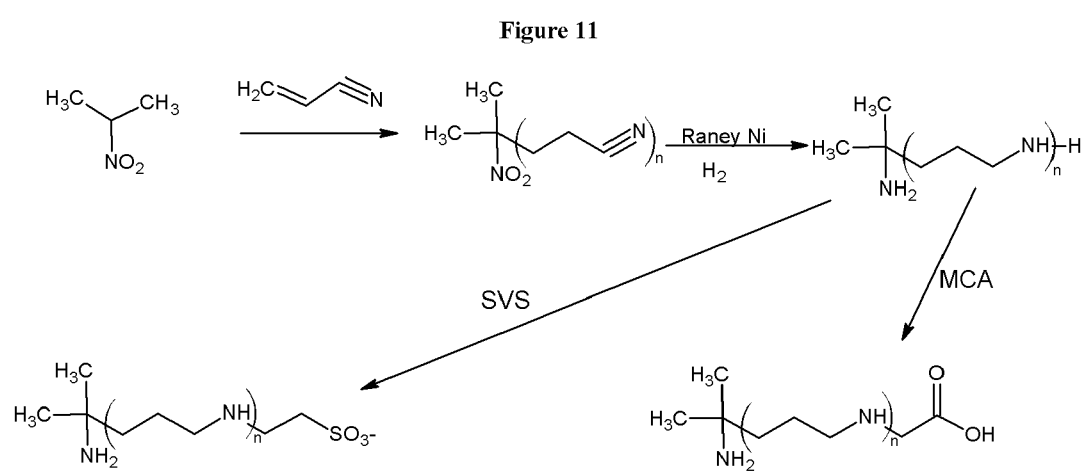
FIG. 11 shows the synthesis of a series of buffers with 2-nitropropane as the starting material.
Figure 12:
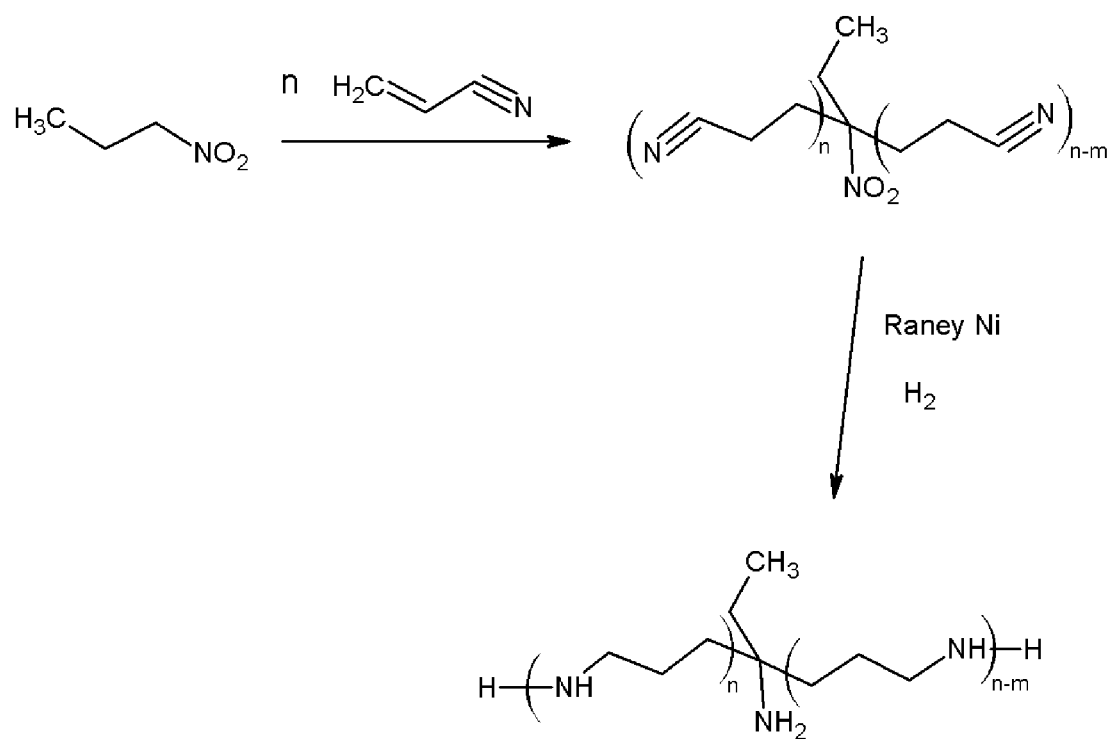
FIG. 12 shows

Polyamines with good properties for use in biological fermentations, purifications, storage and general handling can also be produced through the reaction of nitroalkanes and acrylonitrile, followed by reduction. Additional derivatization with SVS or MCA will result in zwitterionic buffers with a very large buffering range and capacity. FIG. 11 shows the synthesis of a series of buffers with 2-nitropropane as the starting material. FIG. 12 shows the synthesis of a series of buffers with 1-nitropropane as a starting material where n and m are integers where m+n is greater than zero and n is greater than or equal to m. Branching can be imparted on the buffers described in FIGS. 11 through 14 for the polyamines that have greater than 3 amine groups by reducing the resulting nitrile or polynitrile to the polyamine and then reacting with more acrylonitrile and then reducing the resulting nitrile groups to amine groups. This can be done repeatedly. As in FIG. 1, conditions can be chosen such that a more branched product results. A more linear product is produced by simply adding all the acrylonitrile in one step, and then reducing the resulting polynitrile to the polyamine. For FIGS. 12 through 14, the zwitterionic products can be made by adding MCA or SVS as shown in FIGS. 2 through 8.

Figure 13:
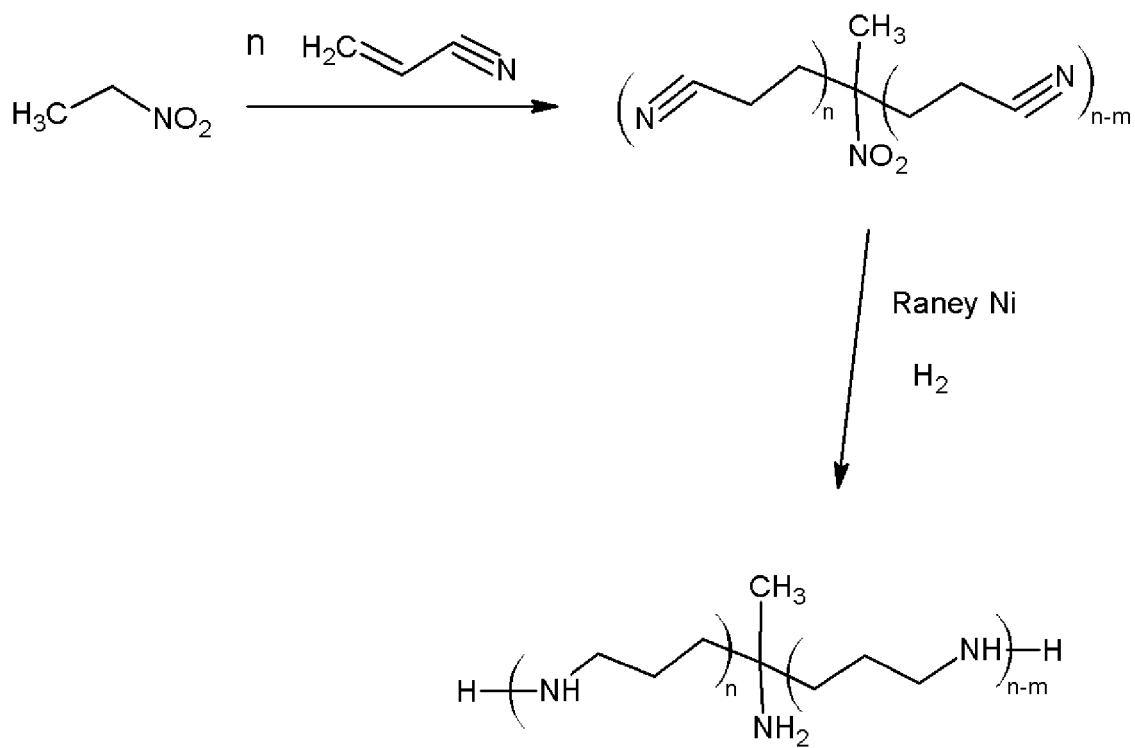
FIG. 13 shows the synthesis of a series of buffers with nitroethane as a starting material where n and m are integers where m+n is greater than zero and n is greater than or equal to m.
Figure 14:
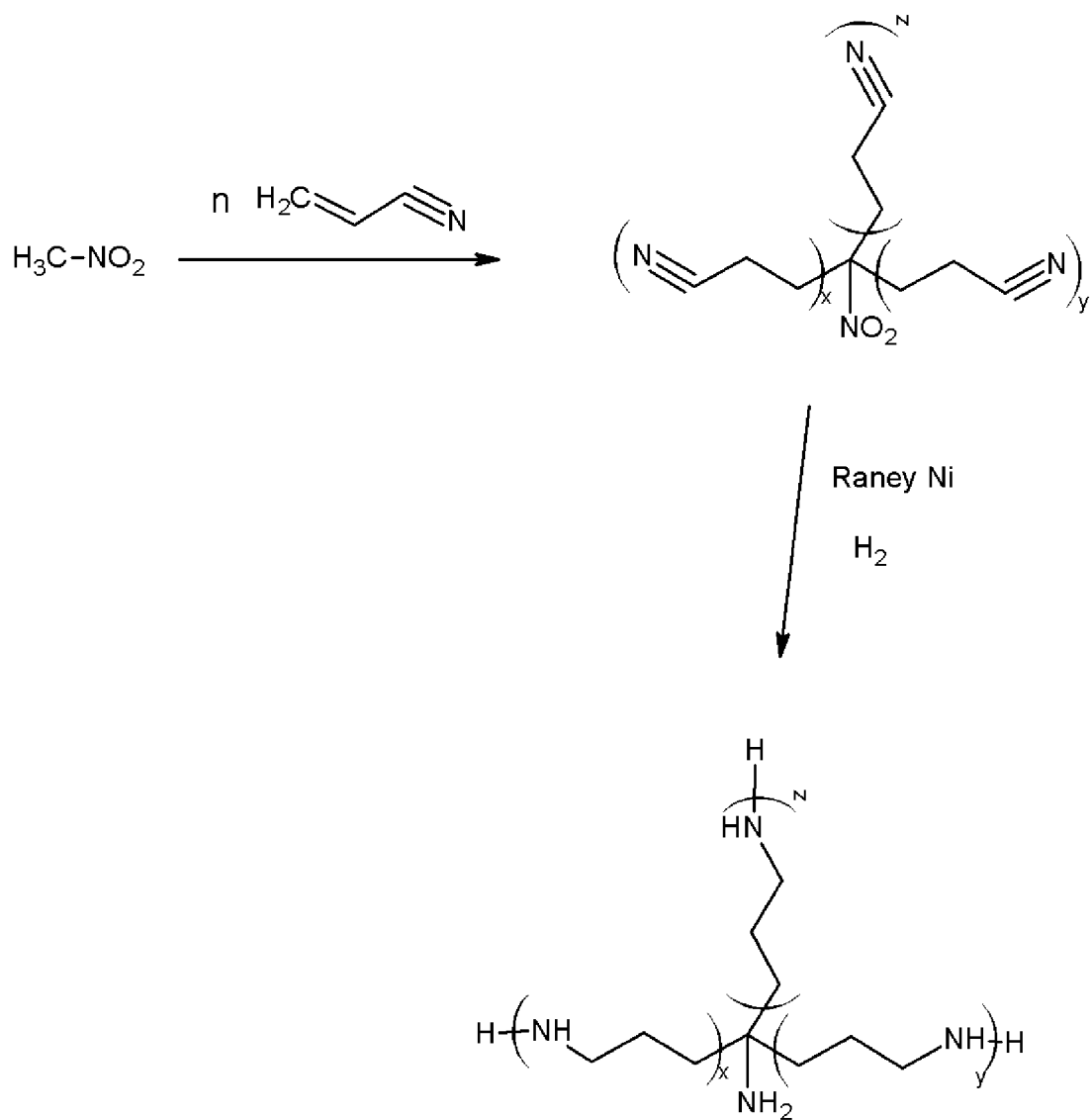
FIG. 14 shows the synthesis of a series of buffers with nitromethane as a starting material where x,y,z and n are integers and x+y+z=n and n is greater than zero.

FIG. 13 shows the synthesis of a series of buffers with nitroethane as a starting material where n and m are integers where m+n is greater than zero and n is greater than or equal to m. FIG. 14 shows the synthesis of a series of buffers with nitromethane as a starting material where x,y,z and n are integers and x+y+z=n and n is greater than zero.

Figure 15:
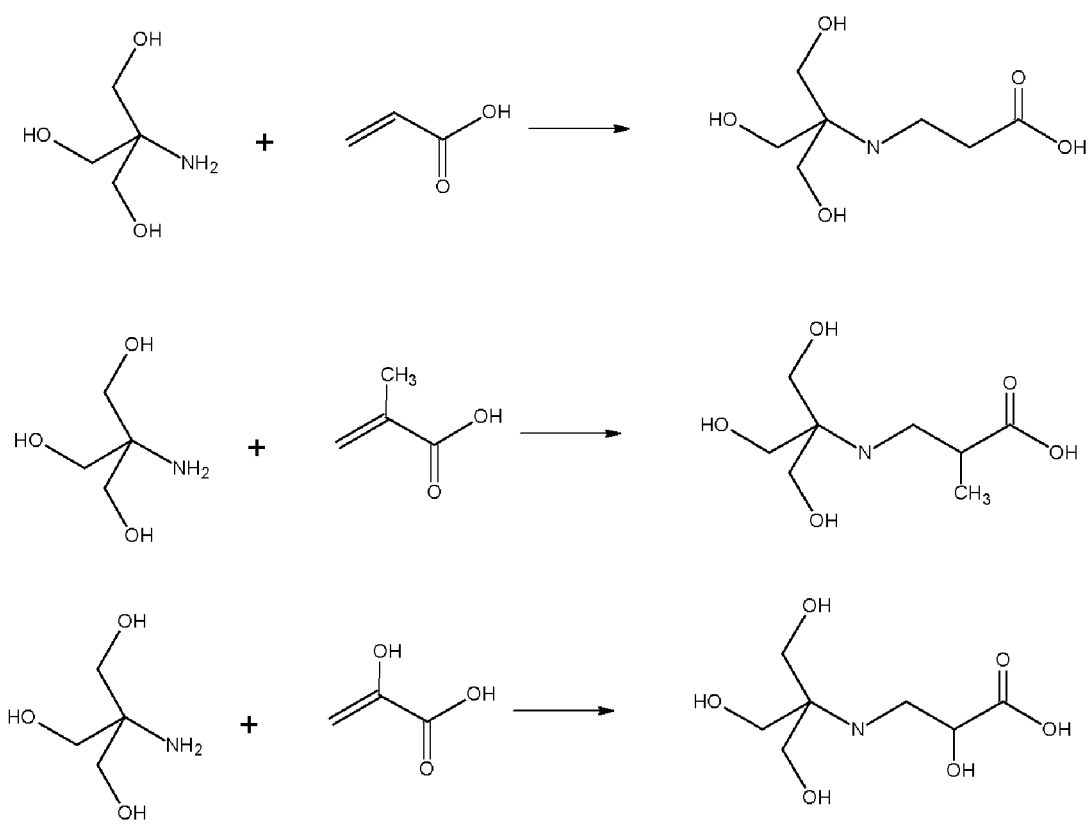
FIG. 15 shows the synthesis of a series of zwitterionic buffers based on acrylic acids.

Another embodiment of the present invention is the synthesis of zwitterionic buffers with vinyl acids. FIG. 15 shows the synthesis of a family of zwitterionic buffers based on members of the acrylic acid family. However, other vinyl acids may be used. Vinyl acids such as acrylic, 3-butenoic acid, 4-pentenoic acid, and other carboxylic acids with a double bond at the terminus. Carboxylic acids with a triple bond at the terminus also can be utilized, similarly, an acid where the multiple bond is not at the terminus, such as hex-4-enoic acid, can also be utilized. However, due to the reduced commercial availability of such compounds, the preferred embodiment is the vinyl acid with a double bond at the terminus. One very large benefit of utilizing vinyl acids to make zwitterionic buffers is that the product does not need to be ion exchanged to produce a non-ionized form. In the market, both ionized, or sometimes called salted, and non-ionized forms sometimes called free acid or free base, are required. In situations where ionic strength must be very closely controlled, the non-ionized forms are more popular. For cases where increased water solubility and ease of solution are desired, the salted forms are preferred. It is understood to one skilled in the art, the present invention covers both the ionized and non-ionized forms of the buffers disclosed herein.

Figure 16:
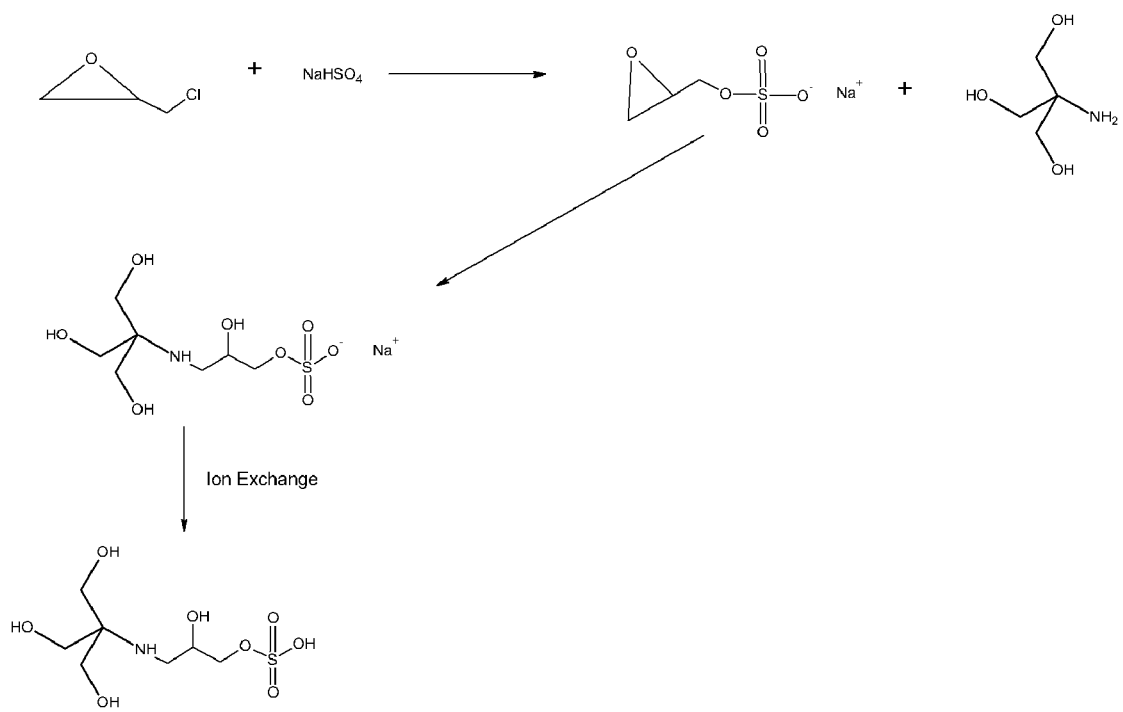
FIG. 16 shows the synthesis of a zwitterionic sulfonate based on tromethamine.
Figure 17:
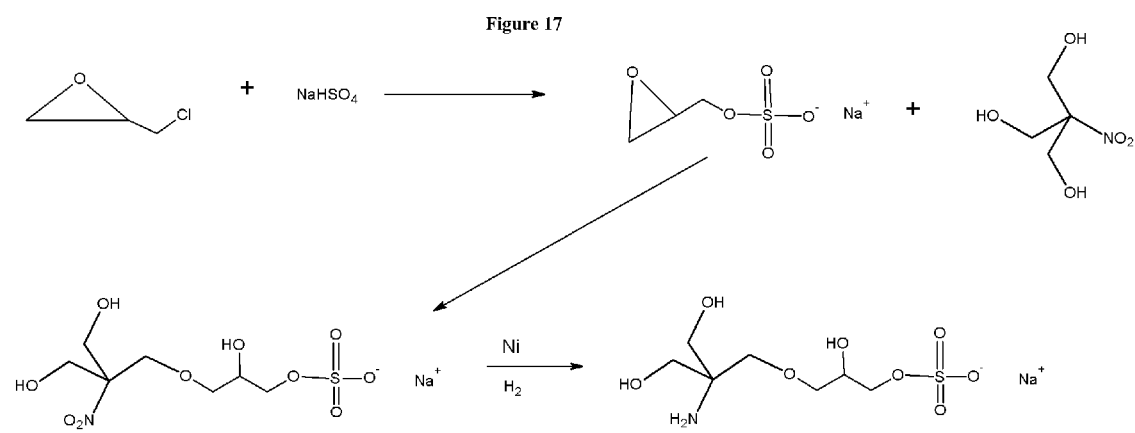
FIG. 17 shows the synthesis of a zwitterionic sulfonate based on aminomethylpropanol.
Figure 18:
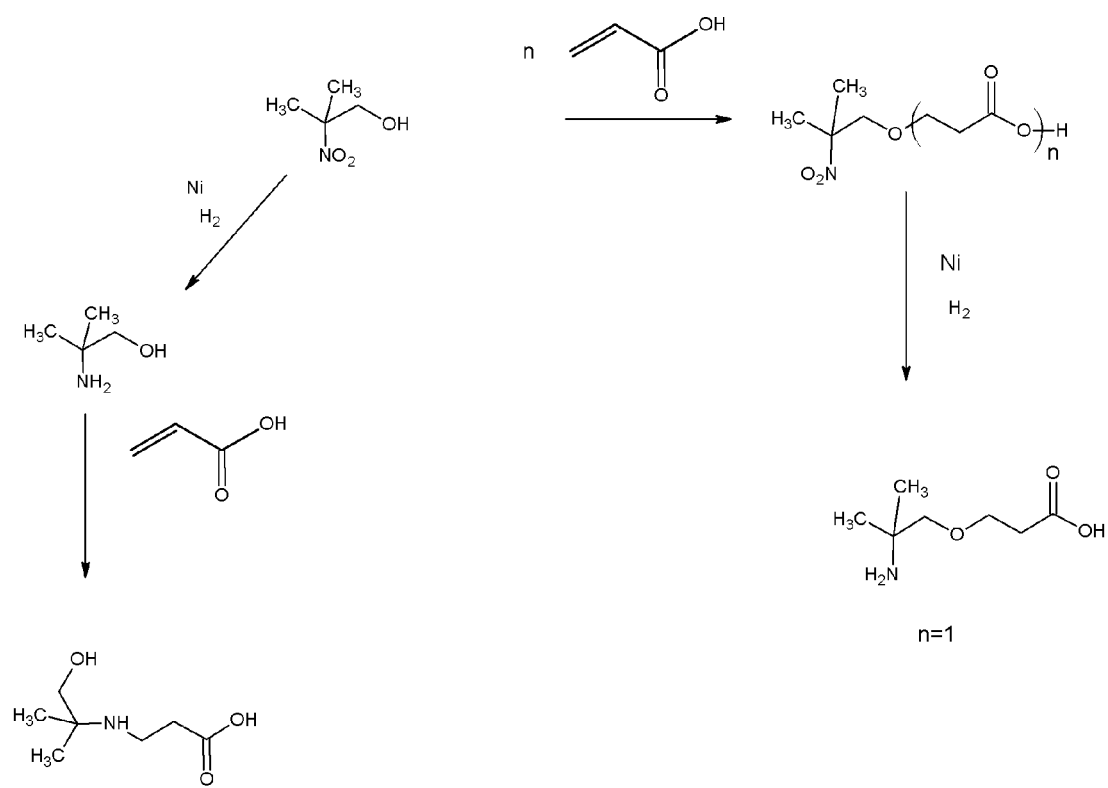
FIG. 18-25 show the synthesis of families of zwitterionic buffers from nitroalcohols.
Figure 19:
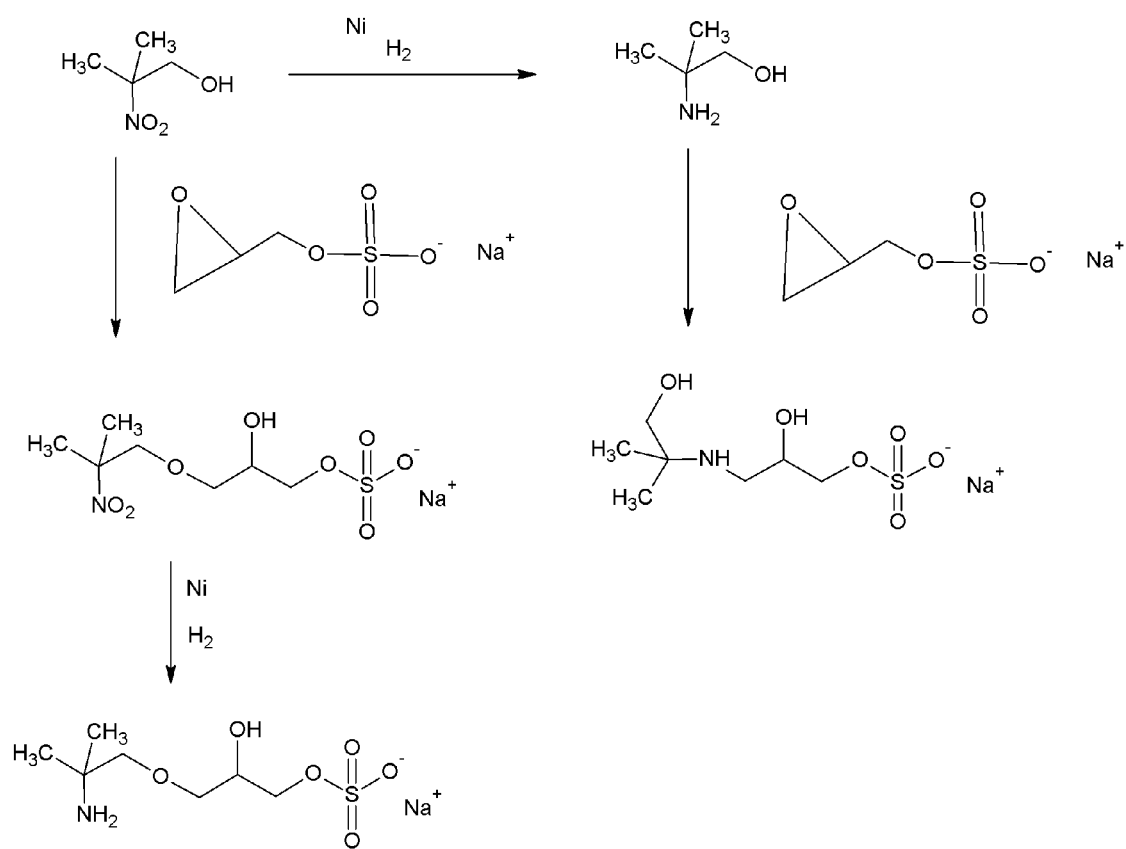
Figure 20:
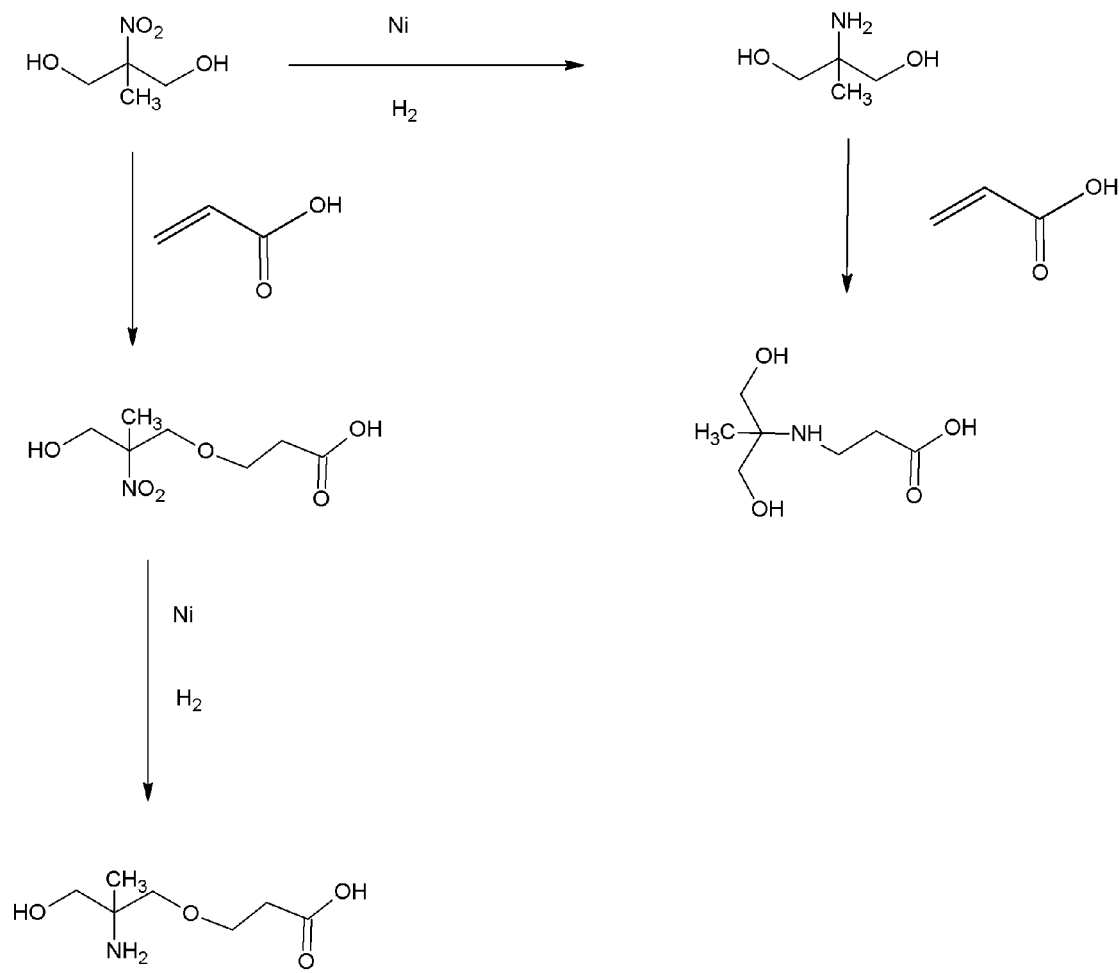
Figure 21:
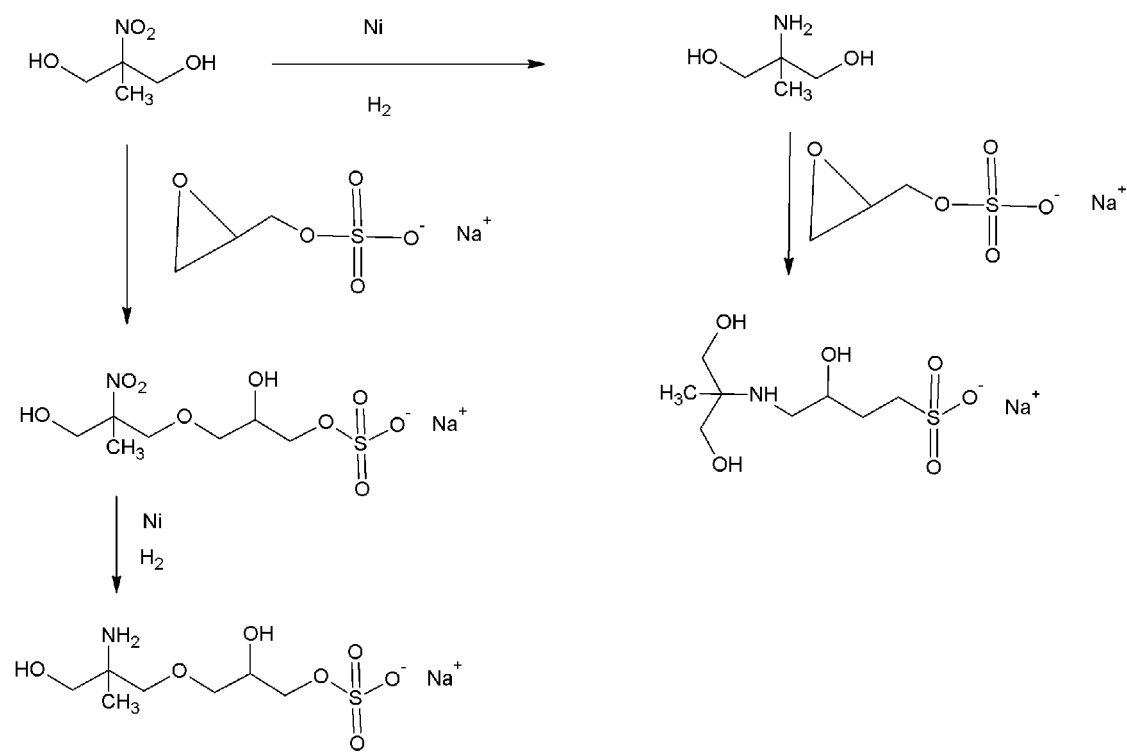
Figure 22:
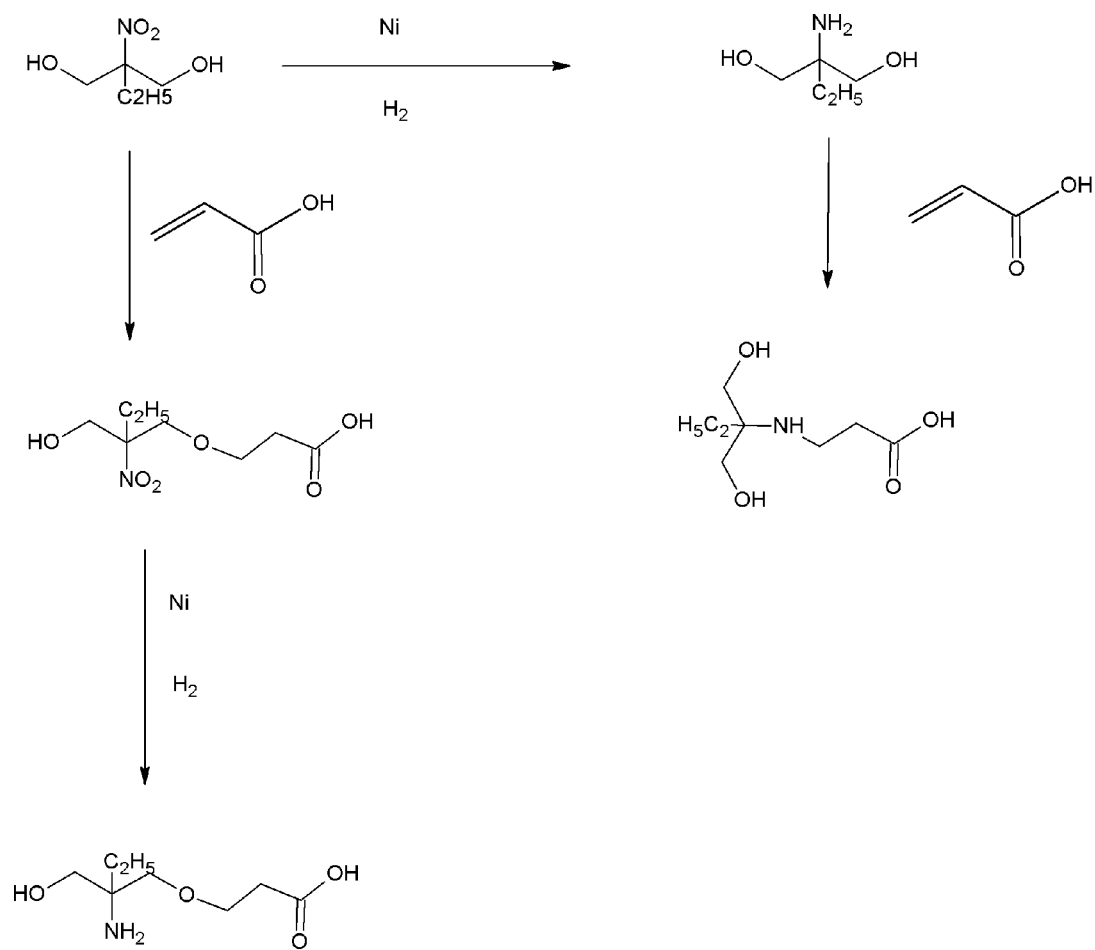
Figure 23:
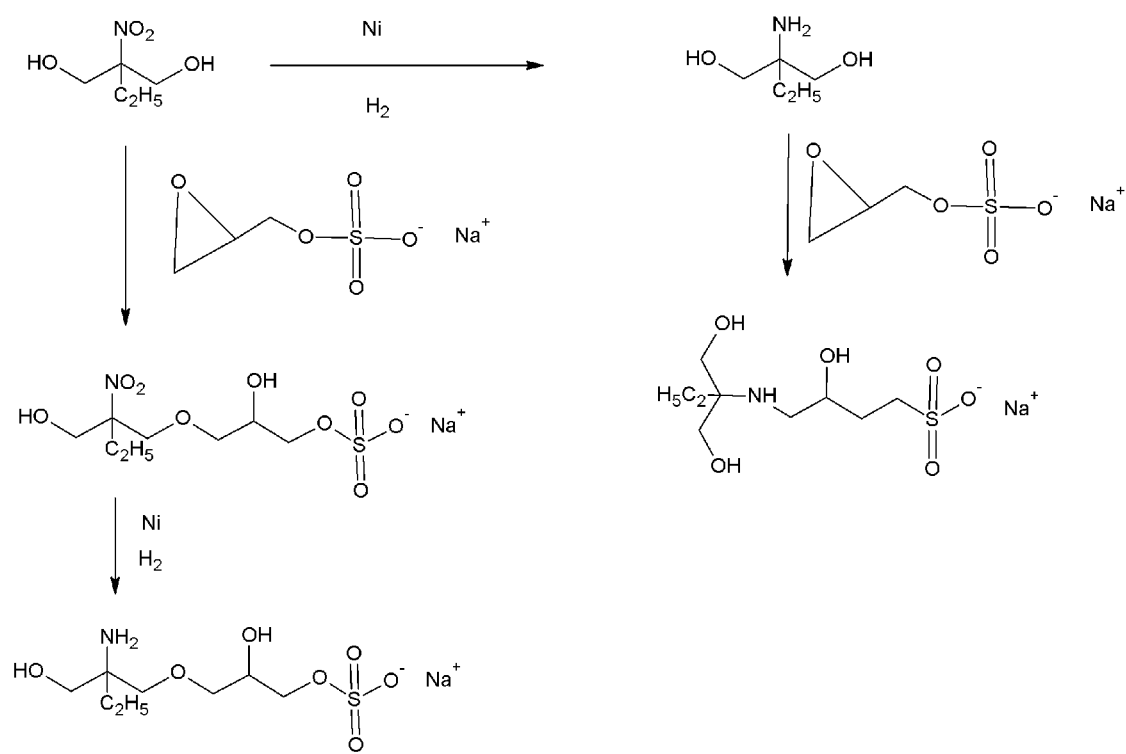
Figure 24:
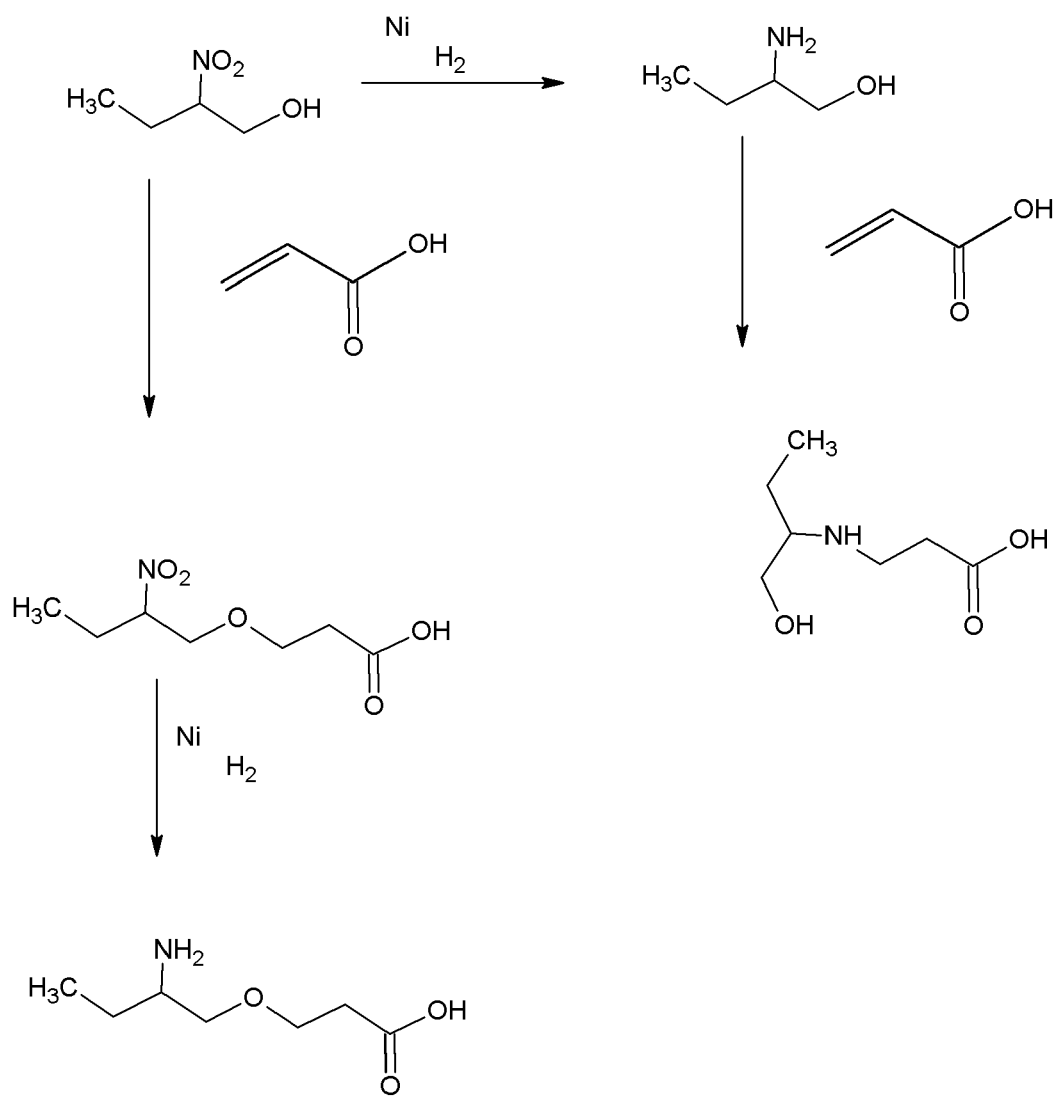
Figure 25:
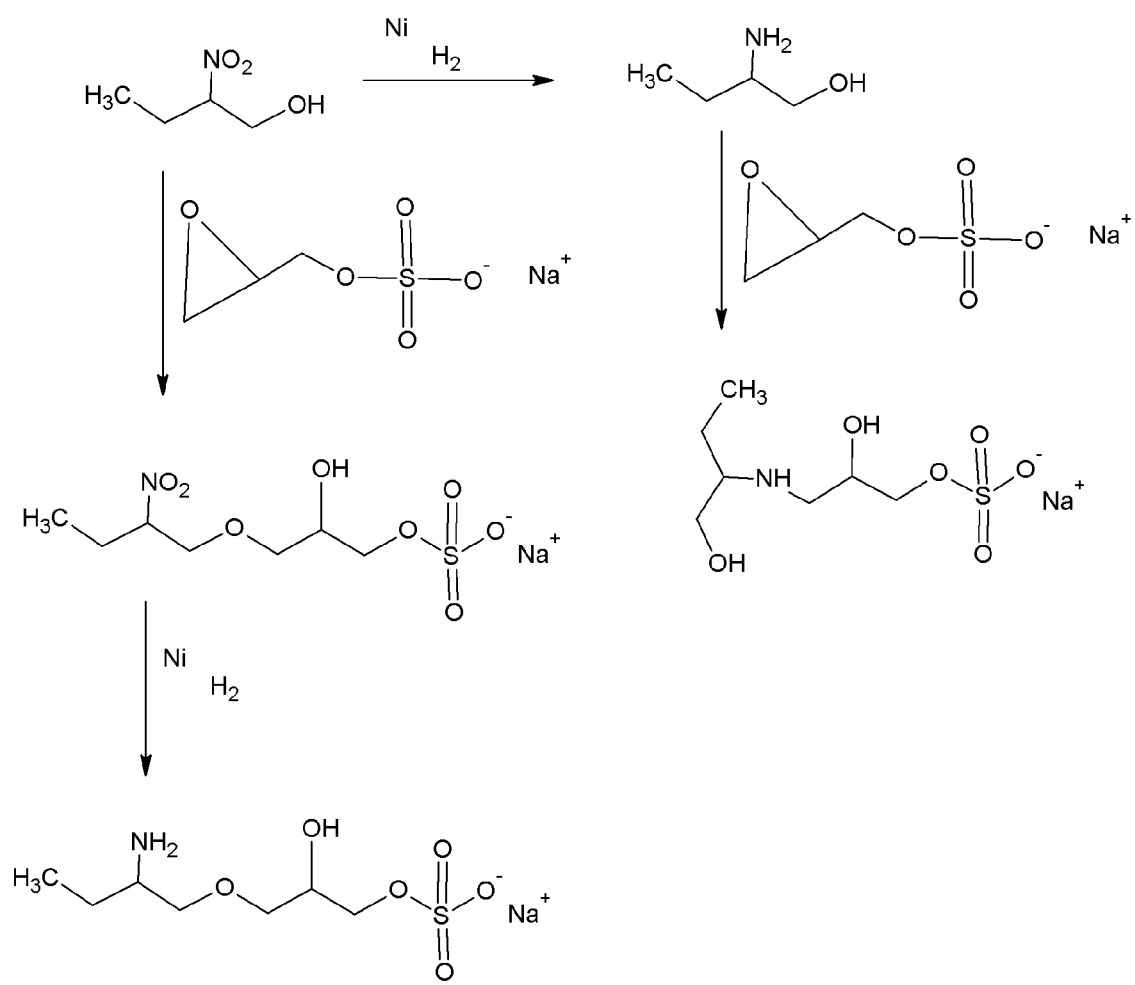

Another embodiment of the present invention is the sulfonate zwitterionic buffers derived from the reaction of an amine with an epichlorohydrin and sodium bisulfate condensate as described in FIG. 16. It is understood by one skilled in the art that other sulfate salts can be utilized to arrive at the desired molecular structure and is included in the present invention. FIGS. 17 through 25 teach the flexibility of the present invention to synthesize a series of a amine sulfonate or amino acid zwitterionic buffers from nitroalcohols or alkanolamines to produce zwitterionic buffers that have primary amino functionality or secondary amino functionality. In cases where there are more than one reactive group, amine, alcohol, or a combination, multiple sulfonate groups or acid groups can be reacted by adding more than one equivalent of the vinyl acid or the oxirane containing sulfonate.

Figure 26:
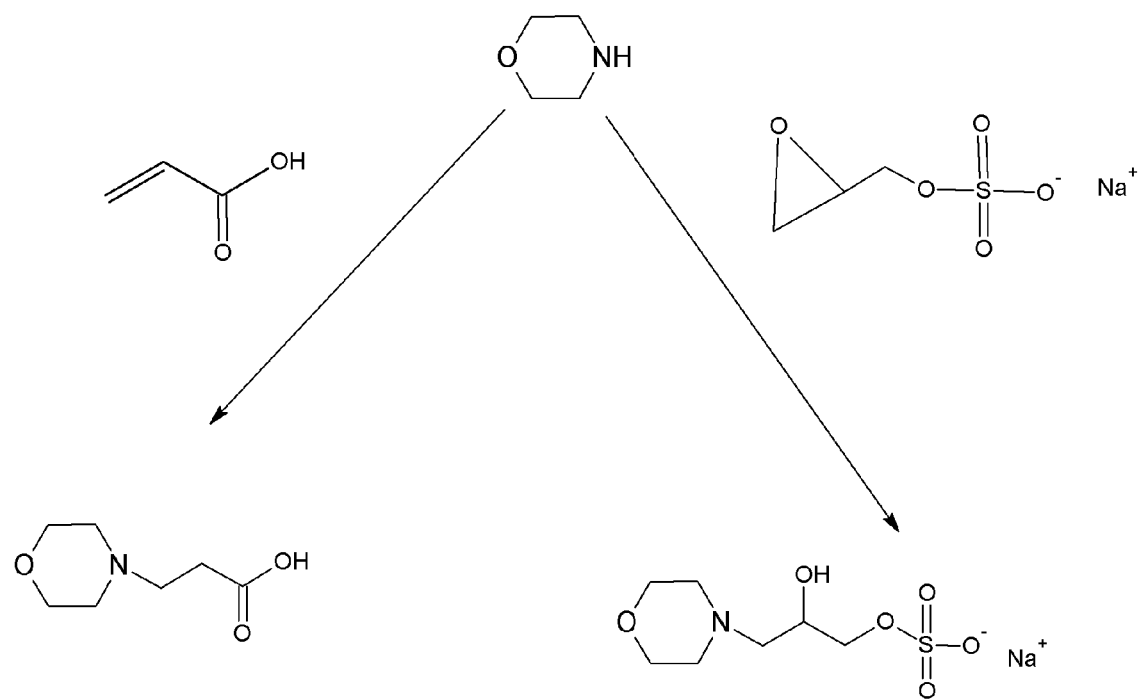
FIG. 26 shows the synthesis of zwitterionic buffers from morpholine.
Figure 27:
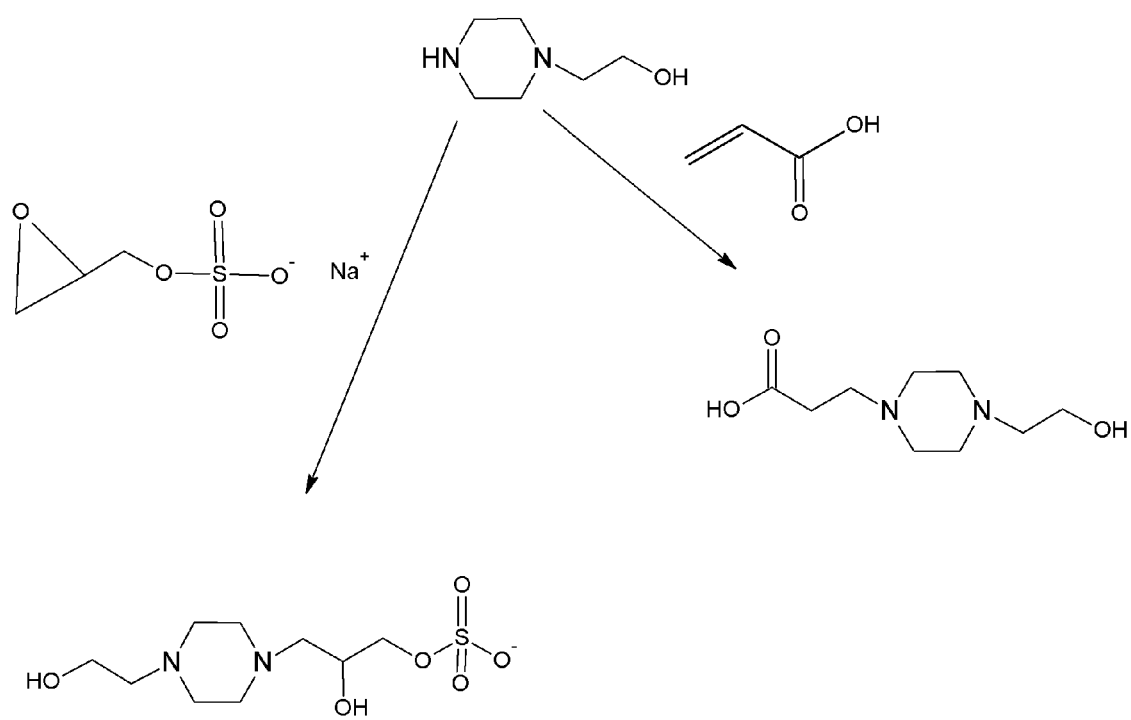
FIG. 27 shows the synthesis of zwitterionic buffers from hydroxyethyl piperazine.
Figure 28:
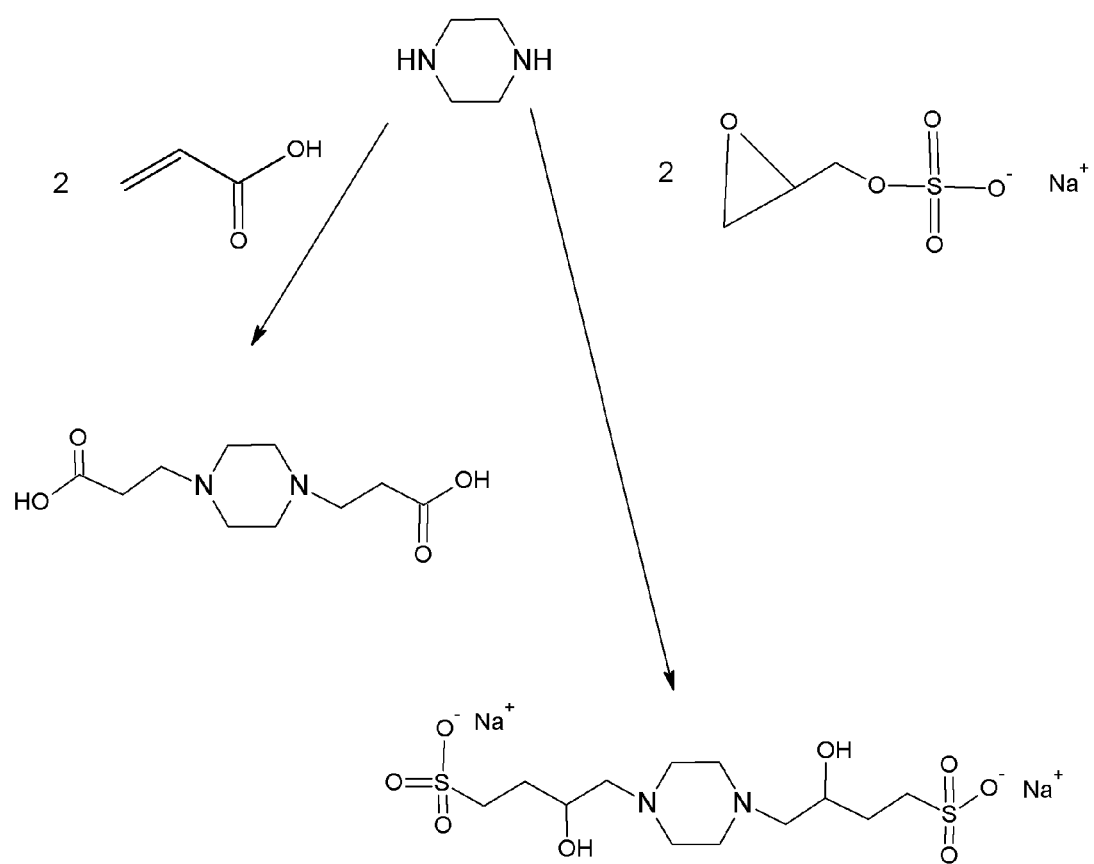
FIG. 28 shows the synthesis of zwitterionic buffers from piperazine.
Figure 29:
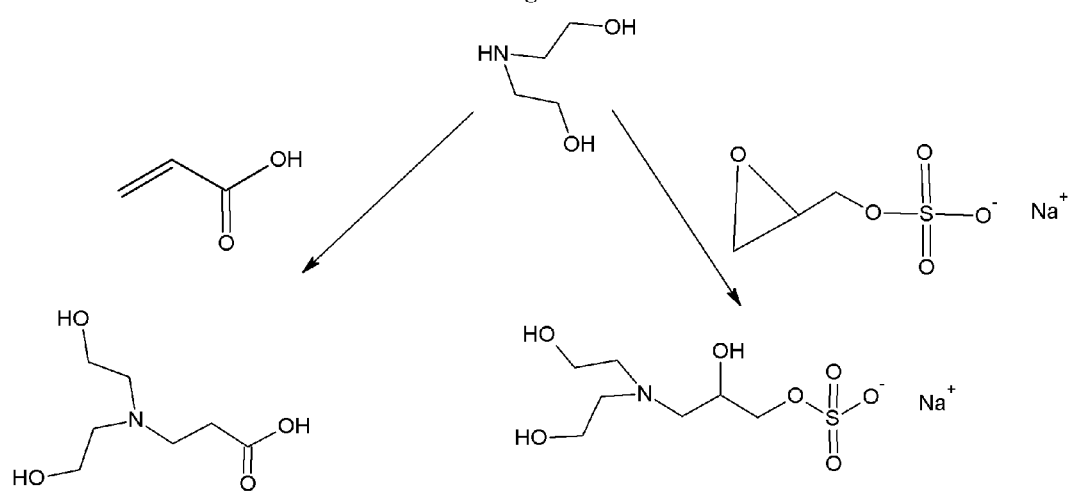
FIG. 29 shows the synthesis of zwitterionic buffers from ethyleneamines.
Figure 29:
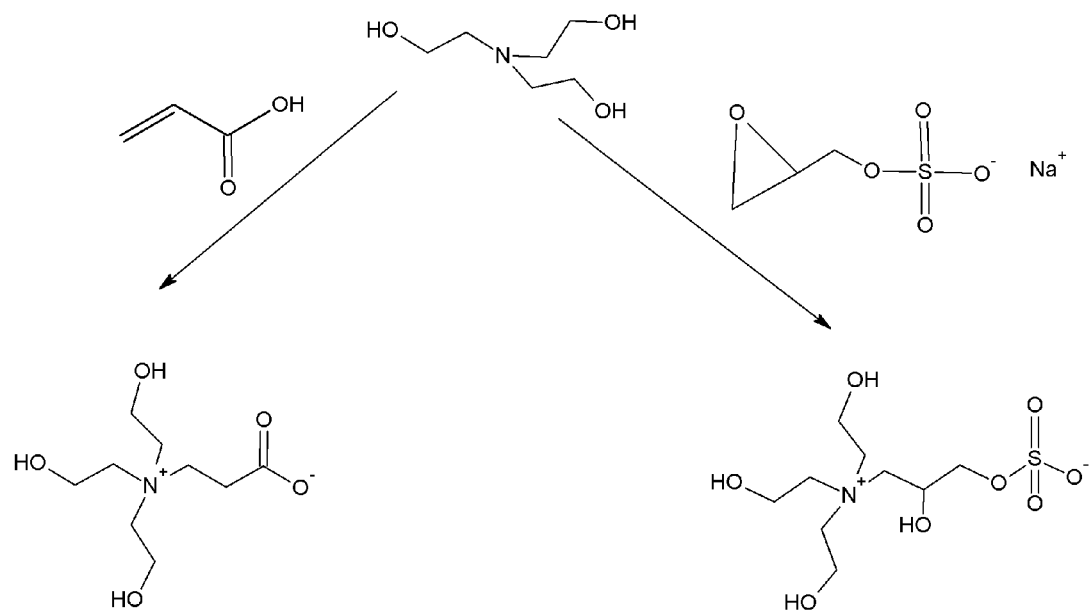

Another embodiment of the current invention is to make zwitterionic buffers with cylcoamines as the starting material. The cycloamines result in a tertiary amino group that is less chelating and interferes less in biological functions. FIG. 26 shows the reaction of morpholine with a vinyl acid and morpholine with the oxirane sulfonate. FIG. 27 teaches similar products, but utilizing hydroxyethyl piperazine. FIG. 28 teaches the use of diamines as starting materials by using piperazine as the starting material. This is a good example of a synthesis of polyzwittterionic buffers as discussed earlier. FIG. 29 teaches the use of ethylene amines to make zwitterionic buffers through reaction with vinyl acids or oxirane sulfonates. One skilled in the art will recognize that similar compounds can be made by using ethylene amines, such as monoethanolamine and the higher homologs, such as diethylenetriamine and is part of the invention disclosed herein.

Figure 30:
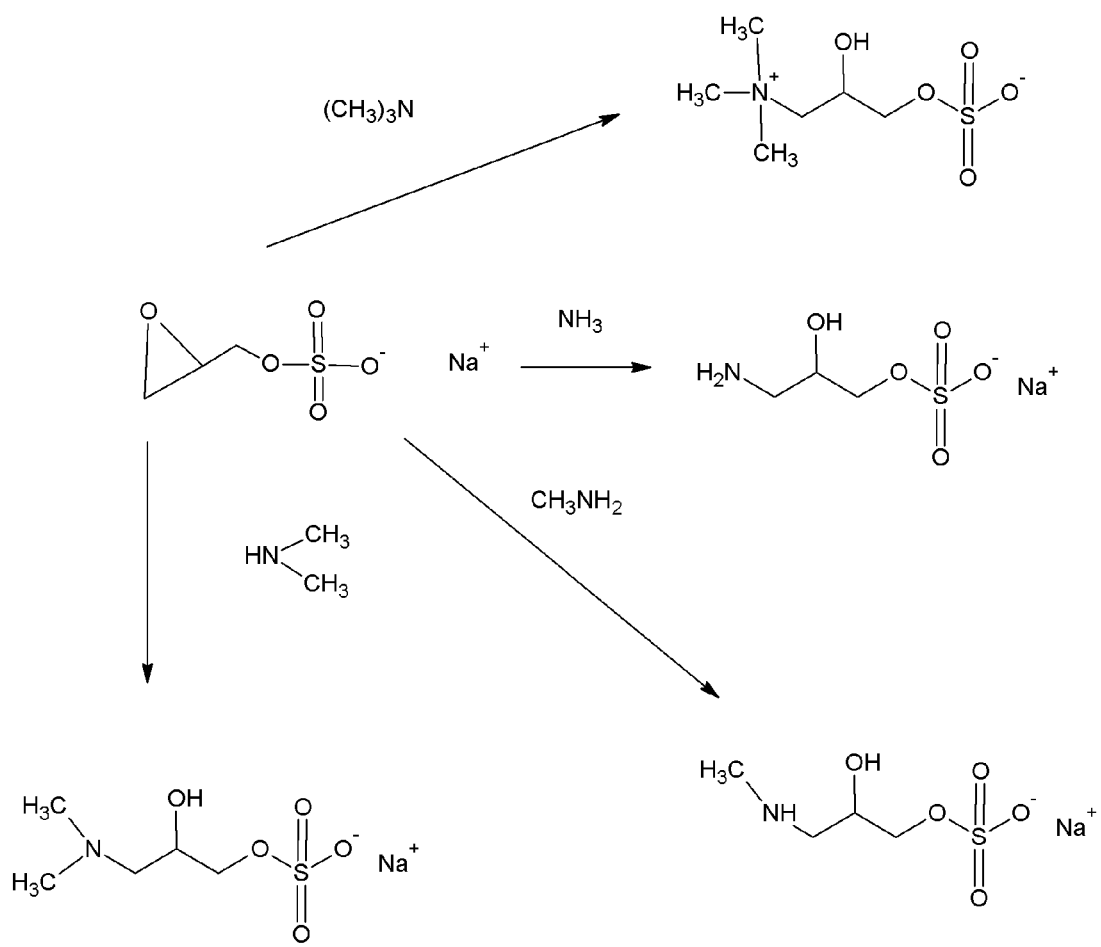
FIG. 30 shows the synthesis of a zwitterionic buffer with primary, secondary, tertiary, or quaternary amine functionality.

Another embodiment of the current invention is the synthesis of zwitterionic amines that have primary, secondary, tertiary, and quaternary amine functionality. FIG. 30 teaches this via oxirane sulfonate and amines. It is obvious to one in the art that any primary, secondary, or tertiary amine can be used in place of the methyamines in FIG. 30. While not shown in the figure, it is obvious to one skilled in the art that the resulting amines can be reacted further with vinyl acids, monochloroacetic acid, sodium vinyl sulfonate, or an oxirane sulfonate to further add acidic character to the zwitterionic buffer.

Figure 31:
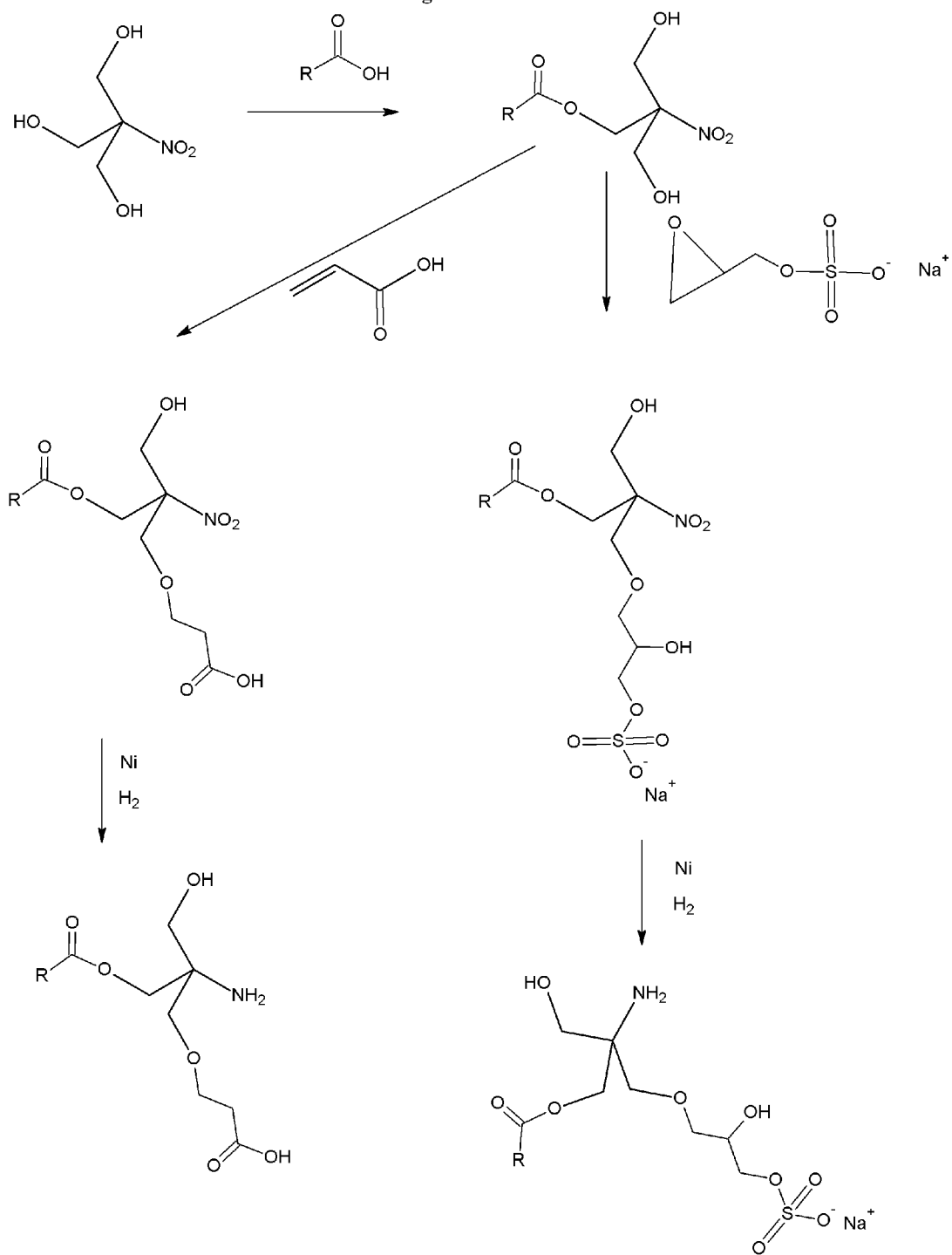
FIGS. 31-33 show the synthesis of mild zwitterionic surfactants from nitroalcohols.
Figure 32:
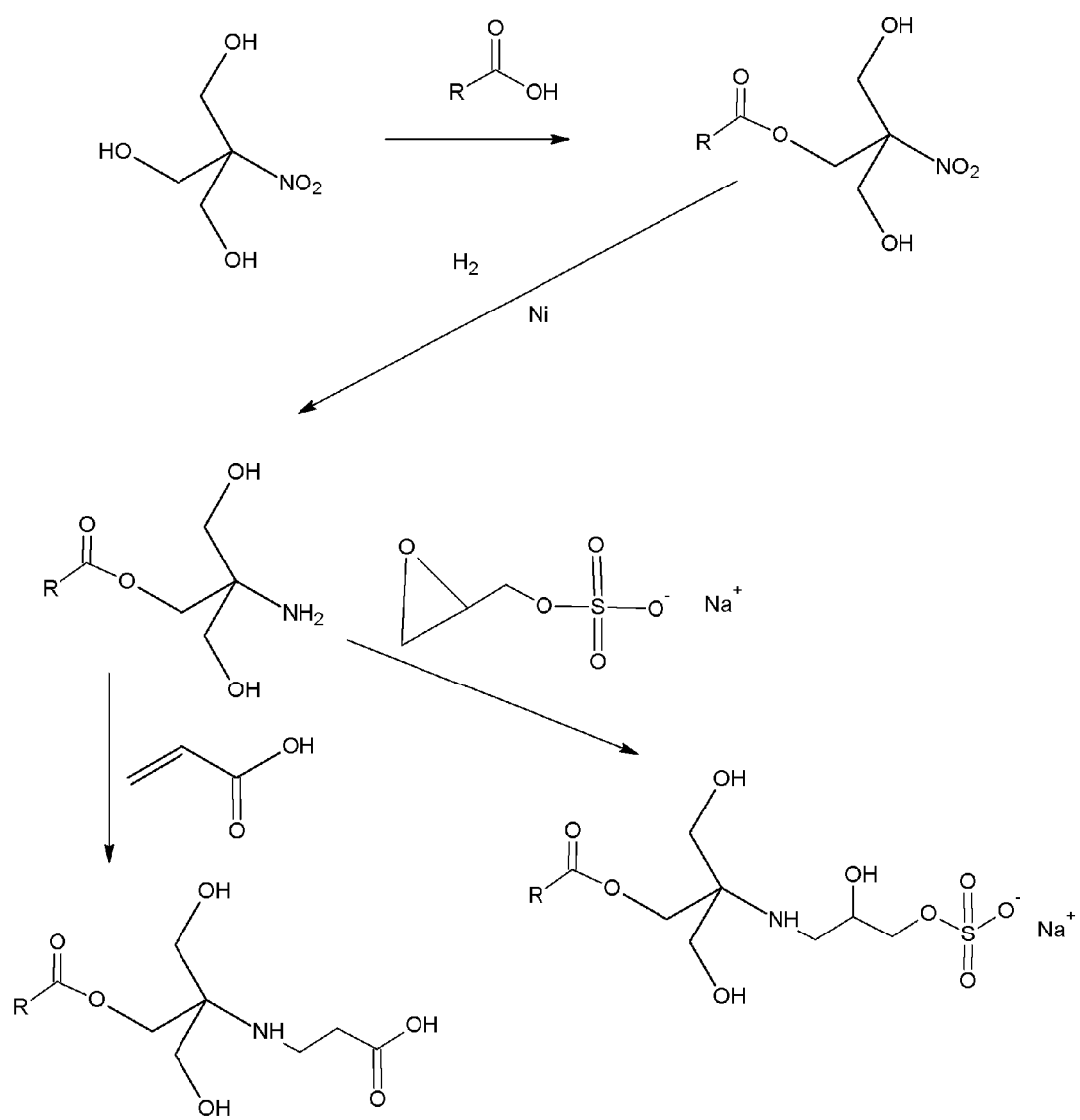
Figure 33:
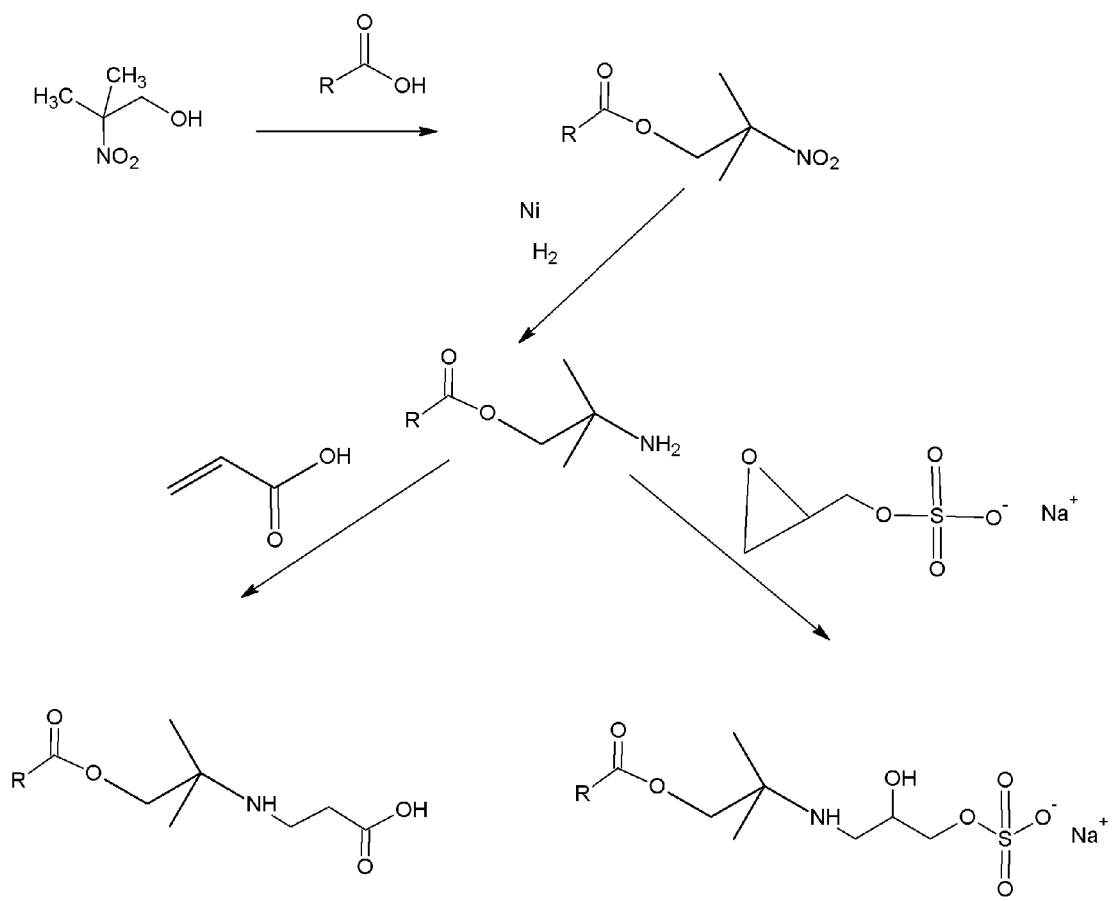

Another embodiment of the current invention is the synthesis of mild surfactants from nitroalcohols. FIGS. 31 through 33 teach the synthesis of these mild surfactants. Lower molecular weight acids produce lower foaming mild surfactants, whereas higher molecular weight carboxylic acids yield higher foam. Lauric acid is the preferred embodiment for a high foaming, mild surfact. Coconut fatty acid performs similarly, but at a lower cost. A good surfactant with low foam can be made using octanoic acid as the carboxcylic acid.

Figure 34:
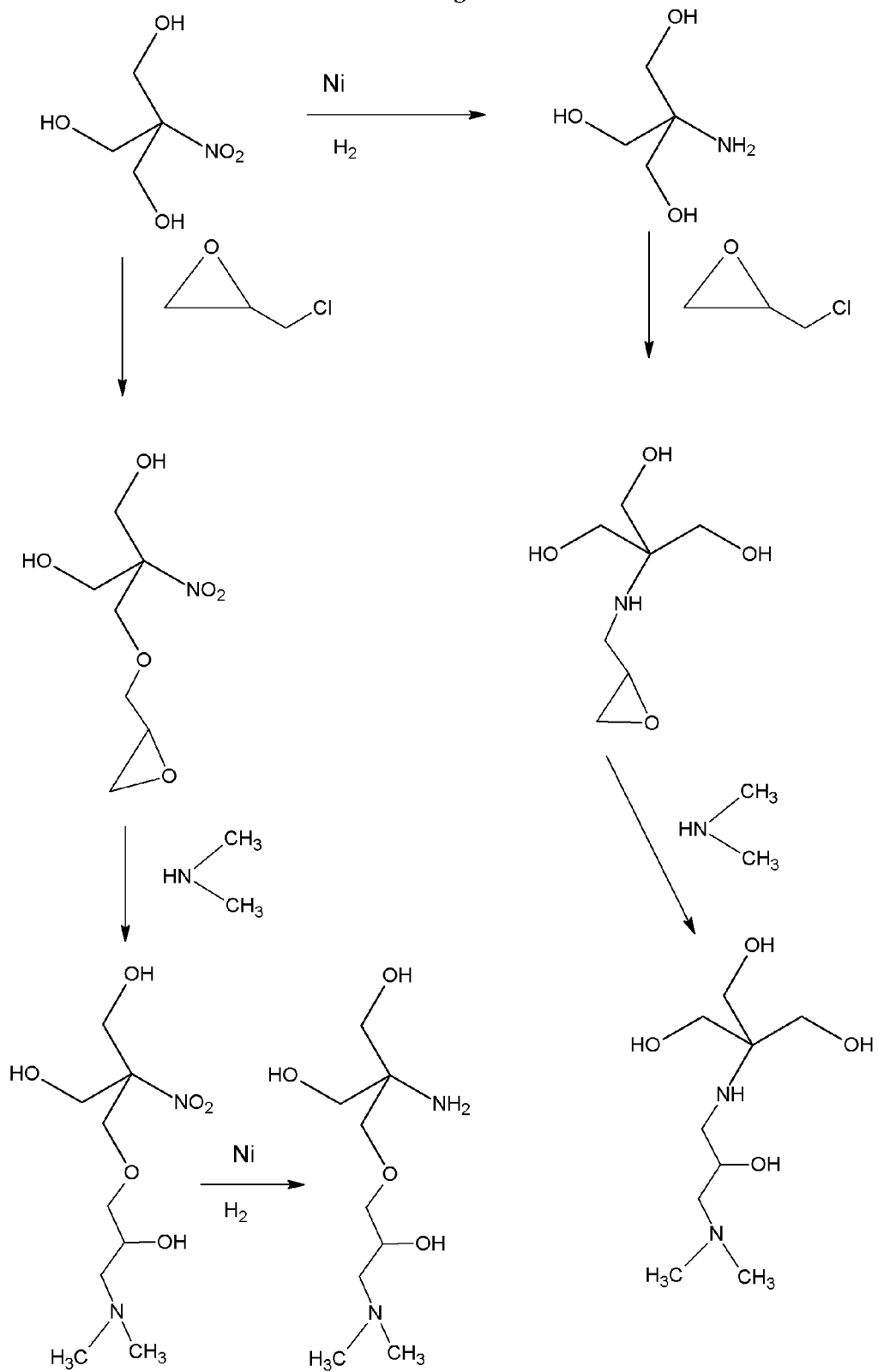
FIG. 34-37 show the synthesis of polyamines from nitroalcohols.
Figure 35:
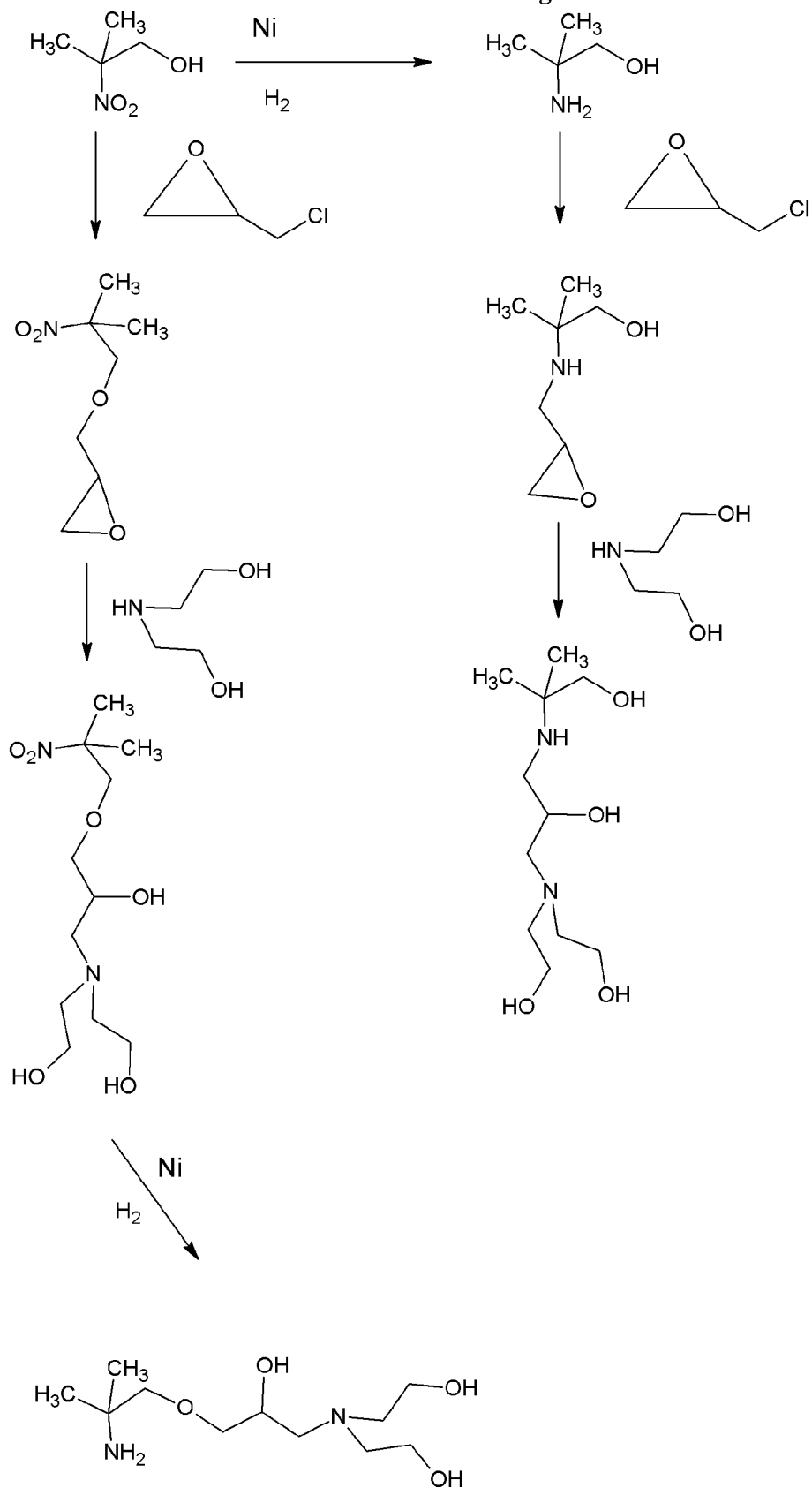
Figure 36:
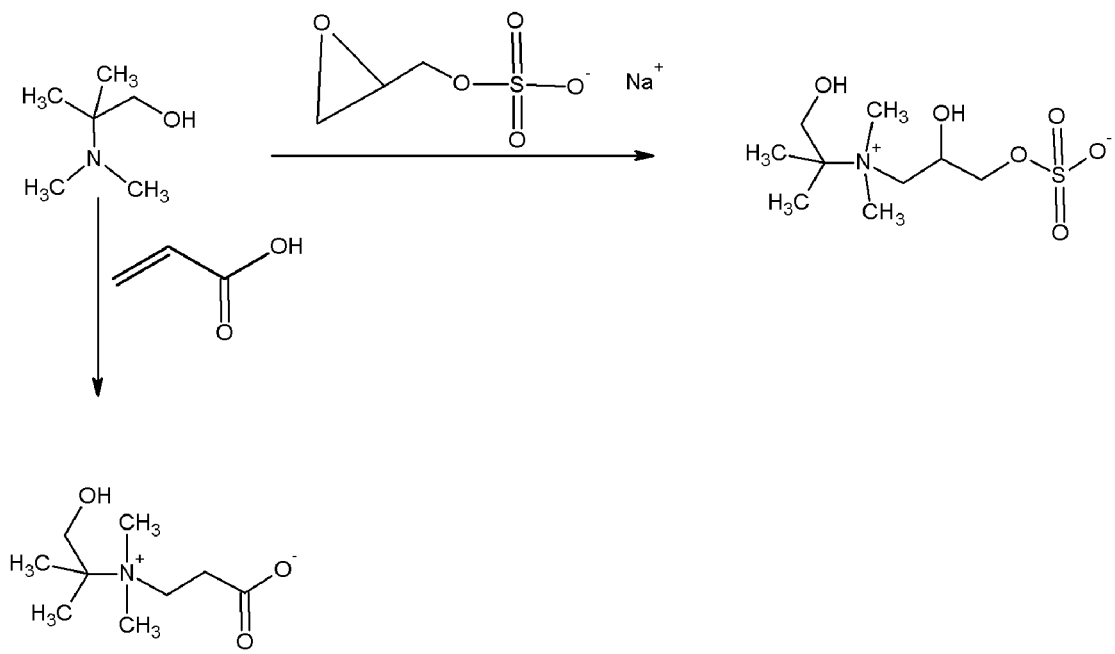
Figure 37:
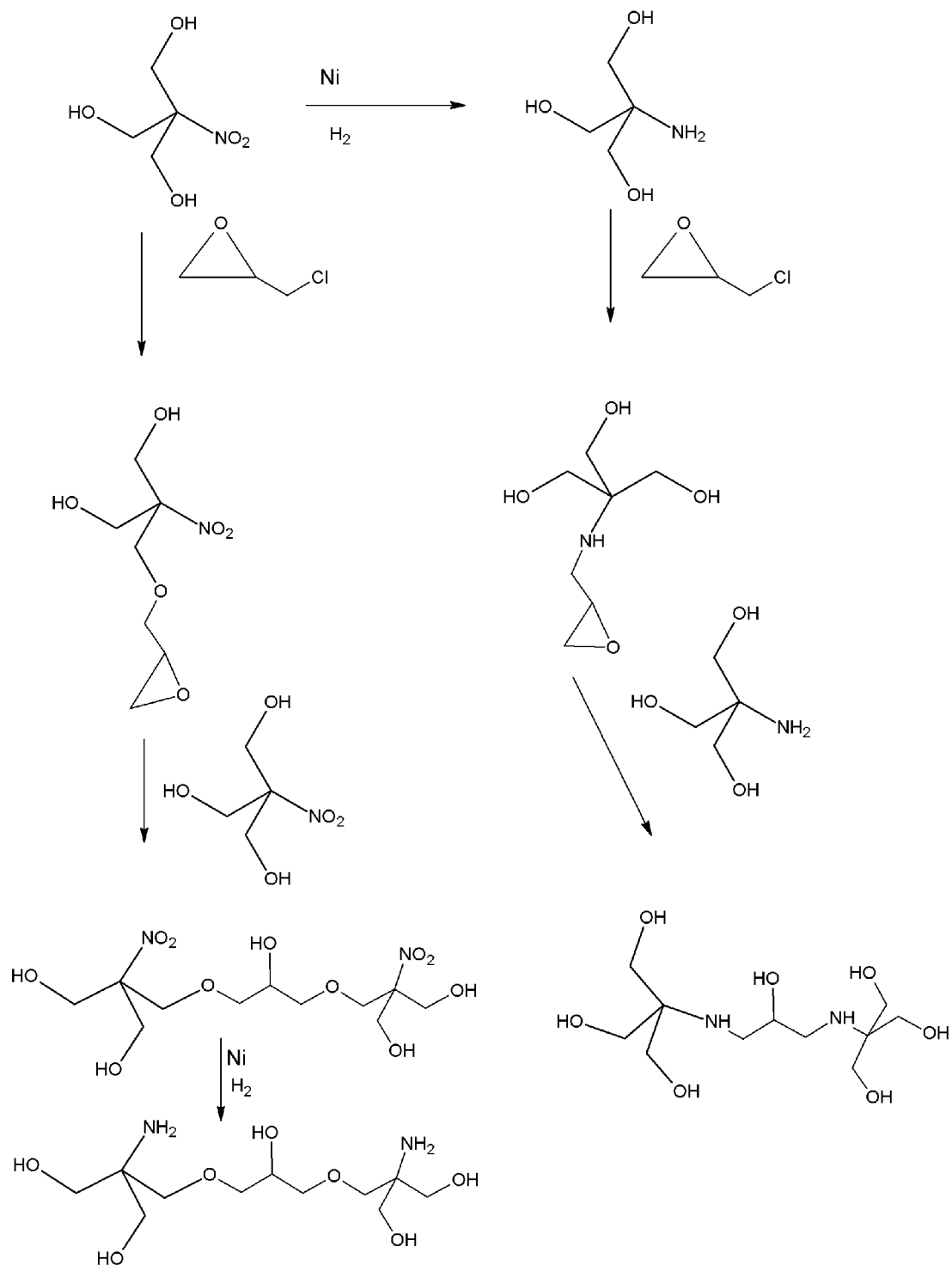
Figure 38:
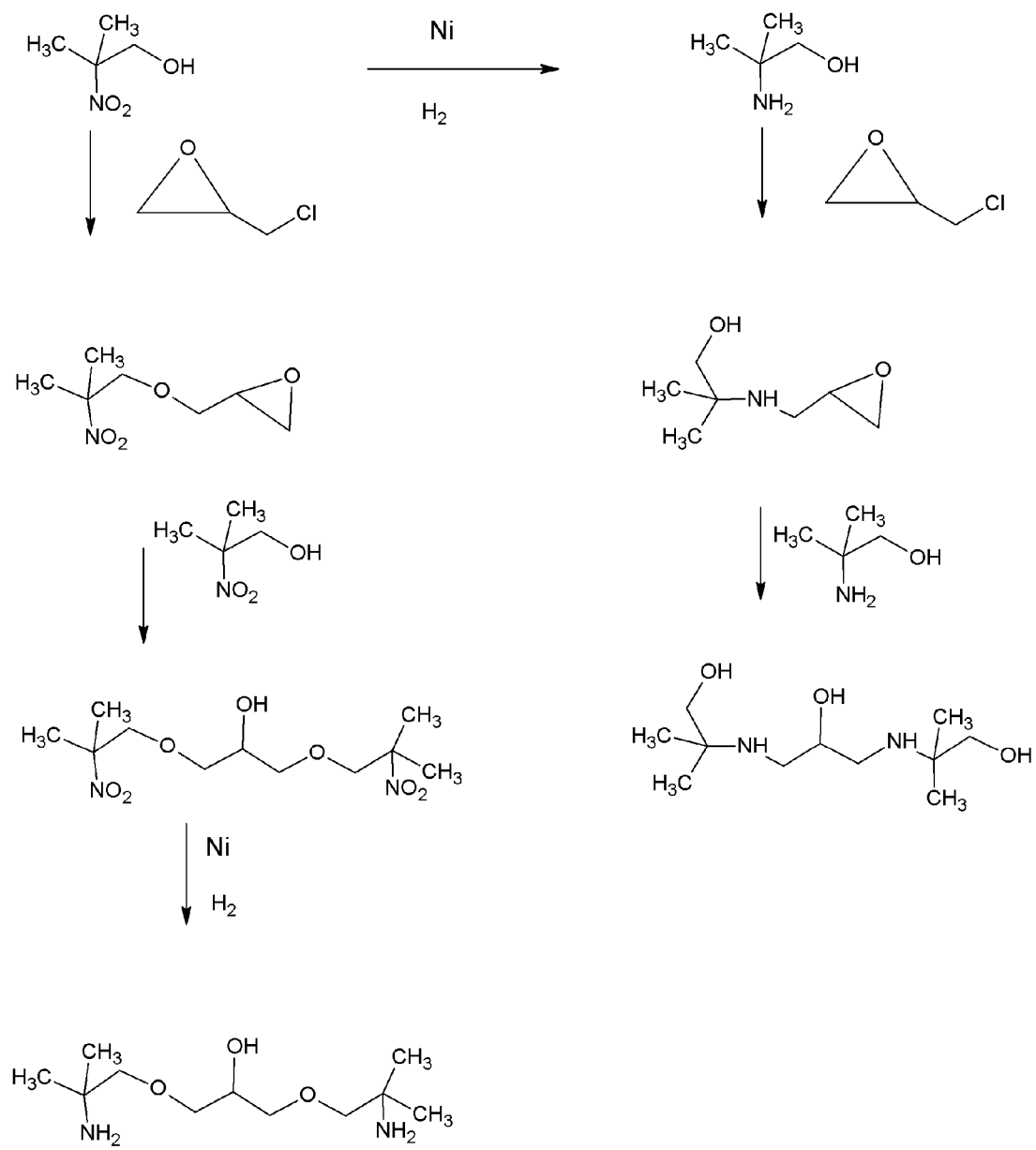
FIG. 38 shows the synthesis of diamines from nitroalcohols and aminoalcohols.
Figure 39:
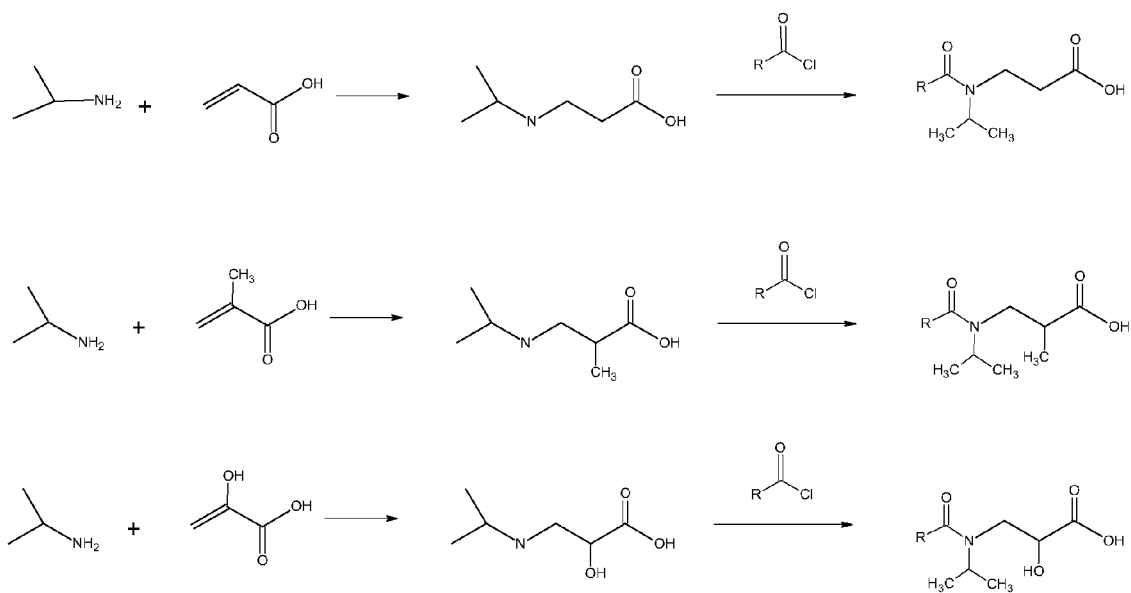
FIG. 39 shows the synthesis of isopropyl amine acrylate buffers and mild surfactants.
Figure 40:
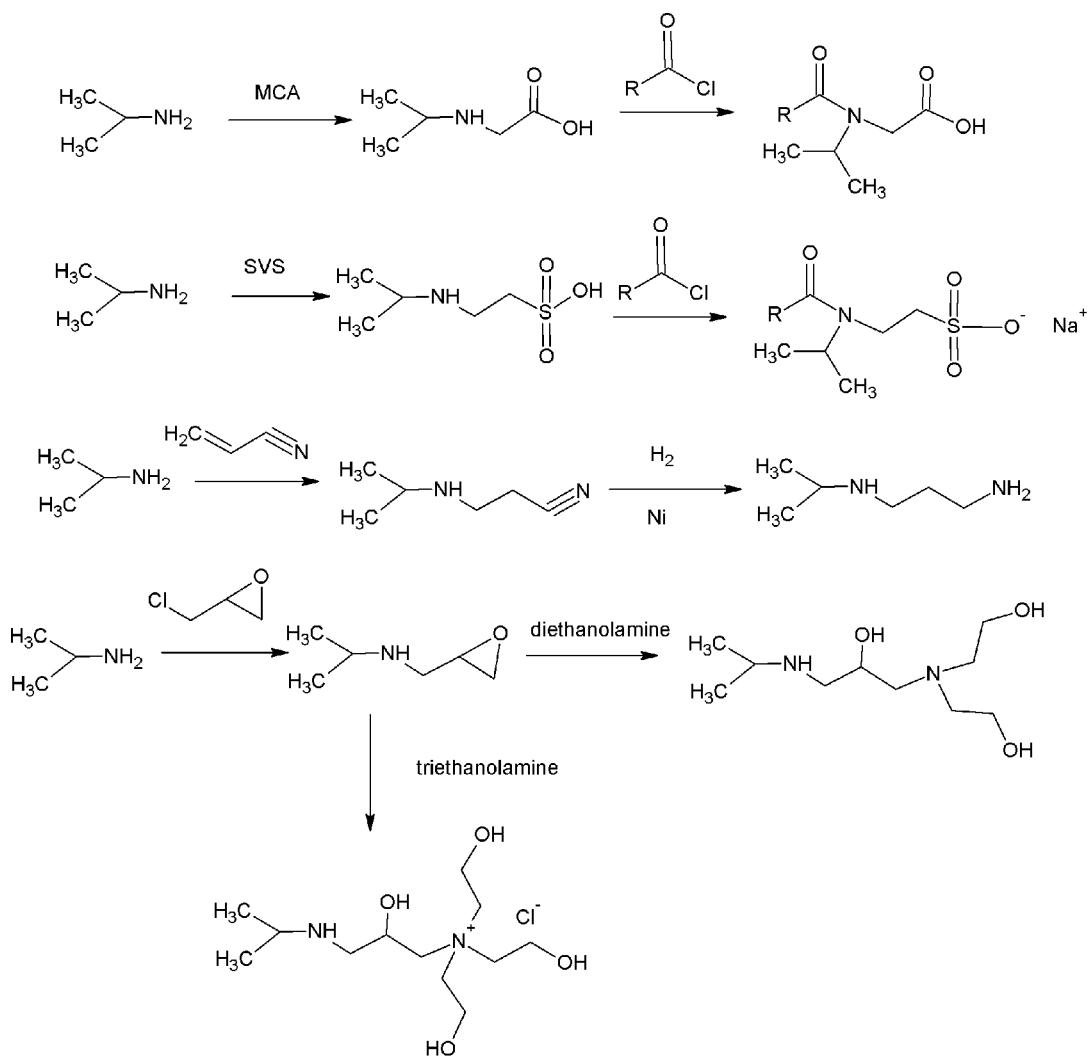
FIG. 40 shows the synthesis of zwitterionic buffers from SVS and MCA derived from isopropyl amine as well as mild surfactants and diamines.
Figure 41:
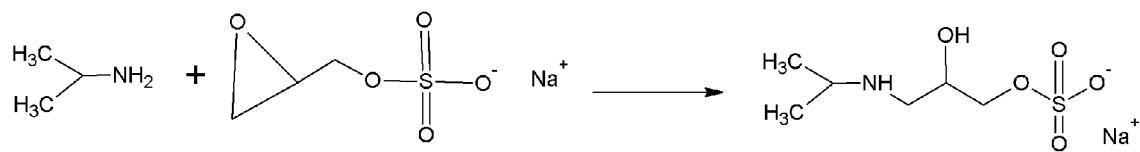
FIG. 41 shows the synthesis of a sultaine zwittterionic buffer of isopropyl amine.

Another embodiment of the current invention is the synthesis of polyamines from nitroalcohols. FIGS. 34 and 35 teach the synthesis of diamines from nitroalcohols. FIG. 34 teaches the synthesis with several hydroxyl groups present. It is understood by one skilled in the art that additional amino groups can be added by reacting more than one equivalent of epichlorohydrin to the nitroalcohol, up to the number of hydroxyl groups, and then reacting the same number of equivalents of amine to the oxirane containing amine. In the case where the nitroalcohol is reduced to the amino alcohol in the beginning, the addition of base, such as caustic, to the amino alcohol will assist in the reaction of the epichlorohydrin with the hydroxyl groups. Without the base, the epichlorohydrin will preferably react with the amine as outlined in the 1 equivelent addition depicted in FIG. 34 and FIG. 35. FIG. 36 demonstrates that tertiary amines can be used to make zwitterionic buffers with quaternary amine functionality from tertiary amines. While not explicitly shown, any other tertiary amine can be used as the starting material and is part of the invention described herein. FIG. 37 and FIG. 38 demonstrate that diamines can be made from nitroalcohols by reacting sequentially the nitroalcohol with epichlorohydrin and then the second equivalent of the nitroalcohol, followed by reduction. Also taught is that a reduction step can take place in the beginning to yield a diamine with two secondary amino groups. It is understood by one skilled in the art that the nitroalcohols or alkanolamines do not need to be symmetric, but others may be used in the synthesis of the diamine and is part of the invention disclosed herein.

Figure 42:
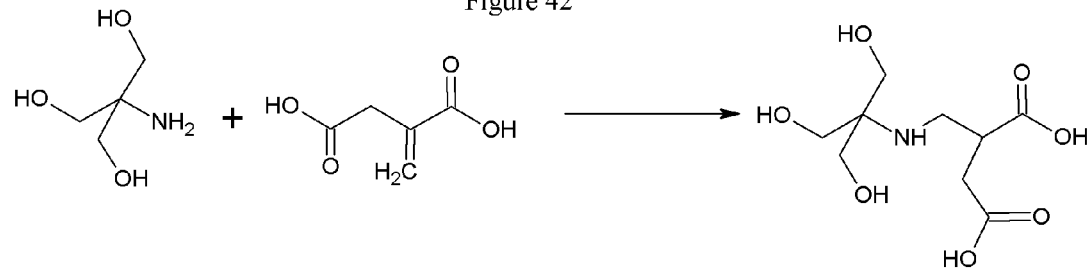
FIG. 42 shows the synthesis of zwitterionic buffers from amino alcohols and itaconic acid.
Figure 42:
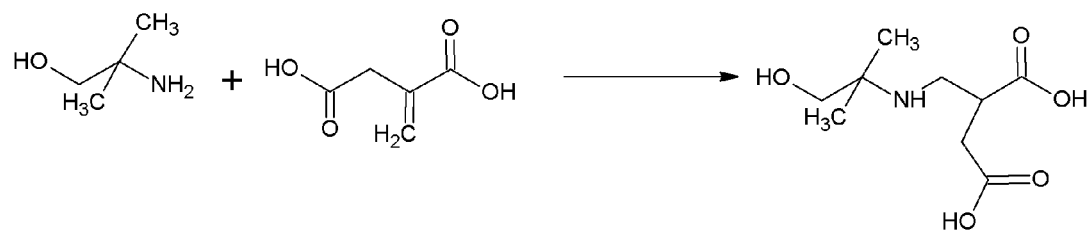
Figure 42:
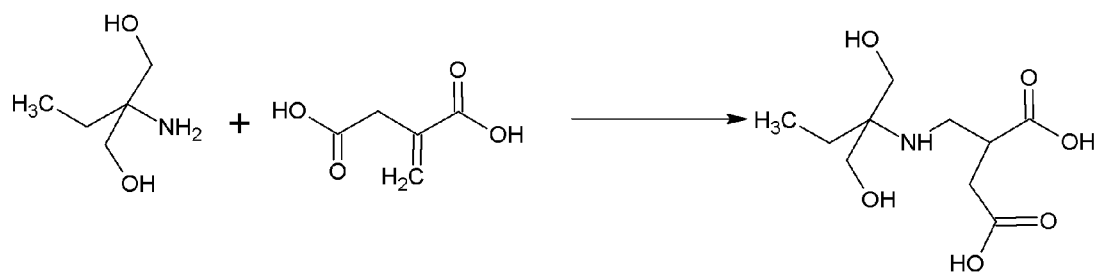
Figure 42:
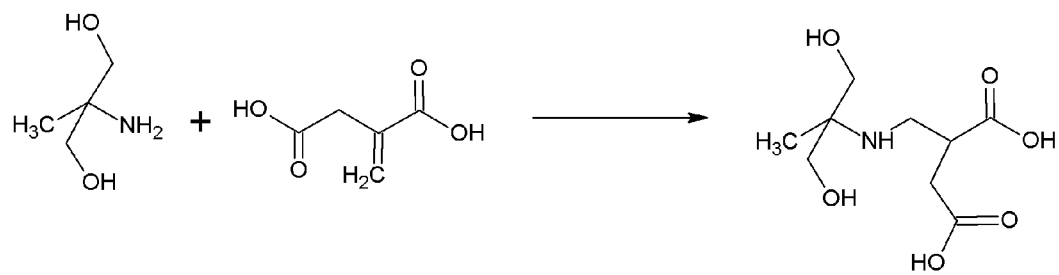
Figure 42:
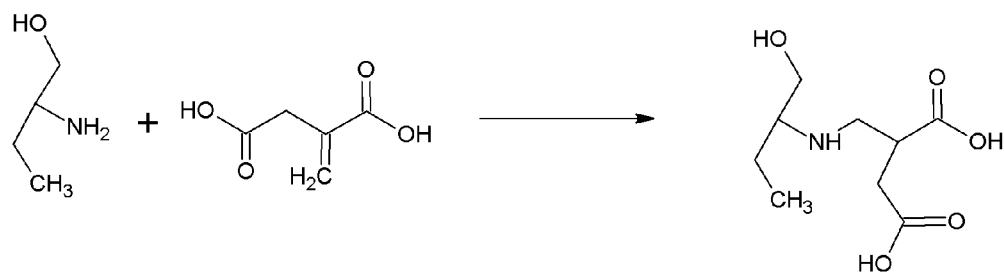
Figure 43:
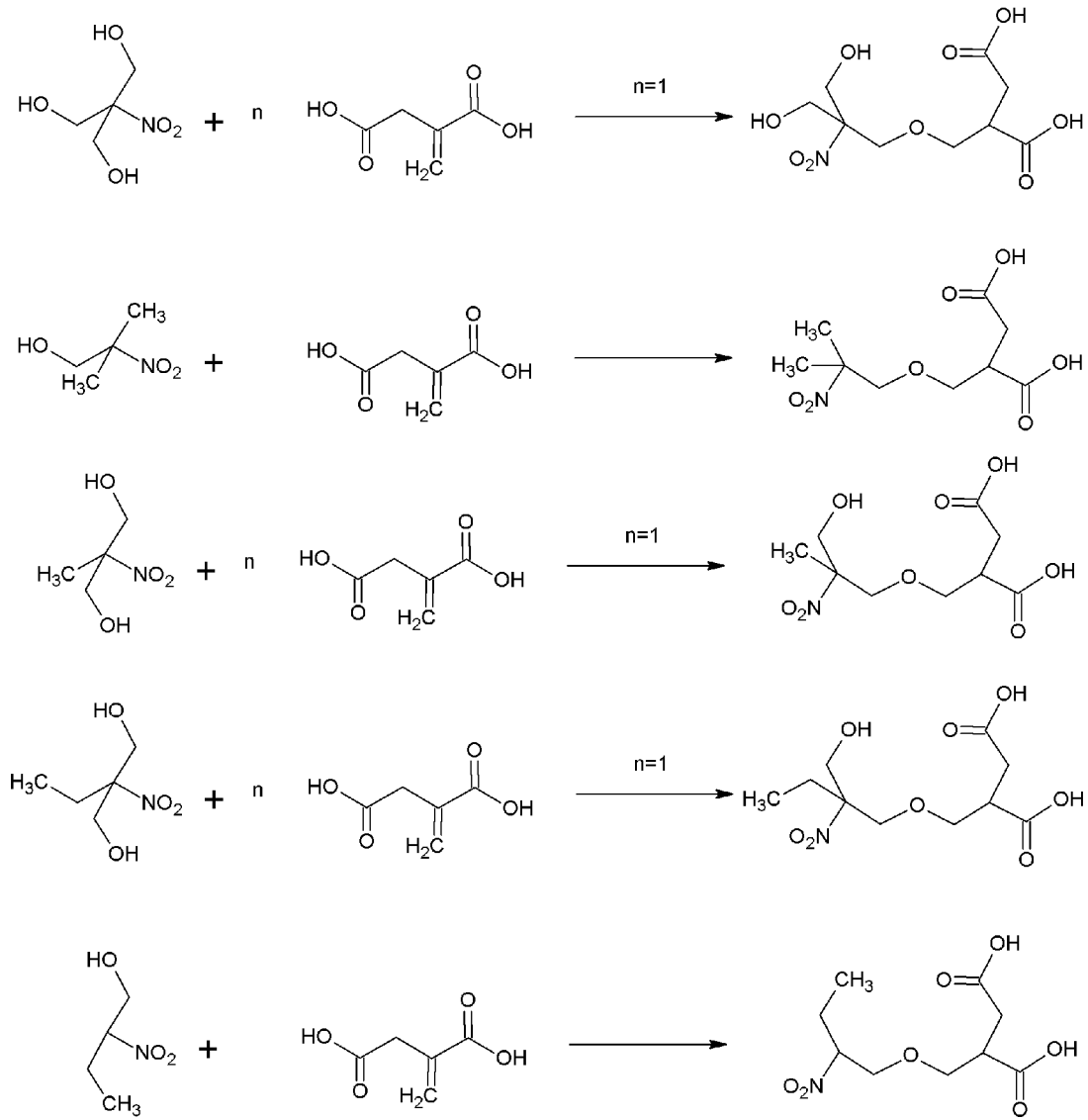
FIG. 43 shows the synthesis of nitro acids from nitroalcohols and itaconic acid.
Figure 44:
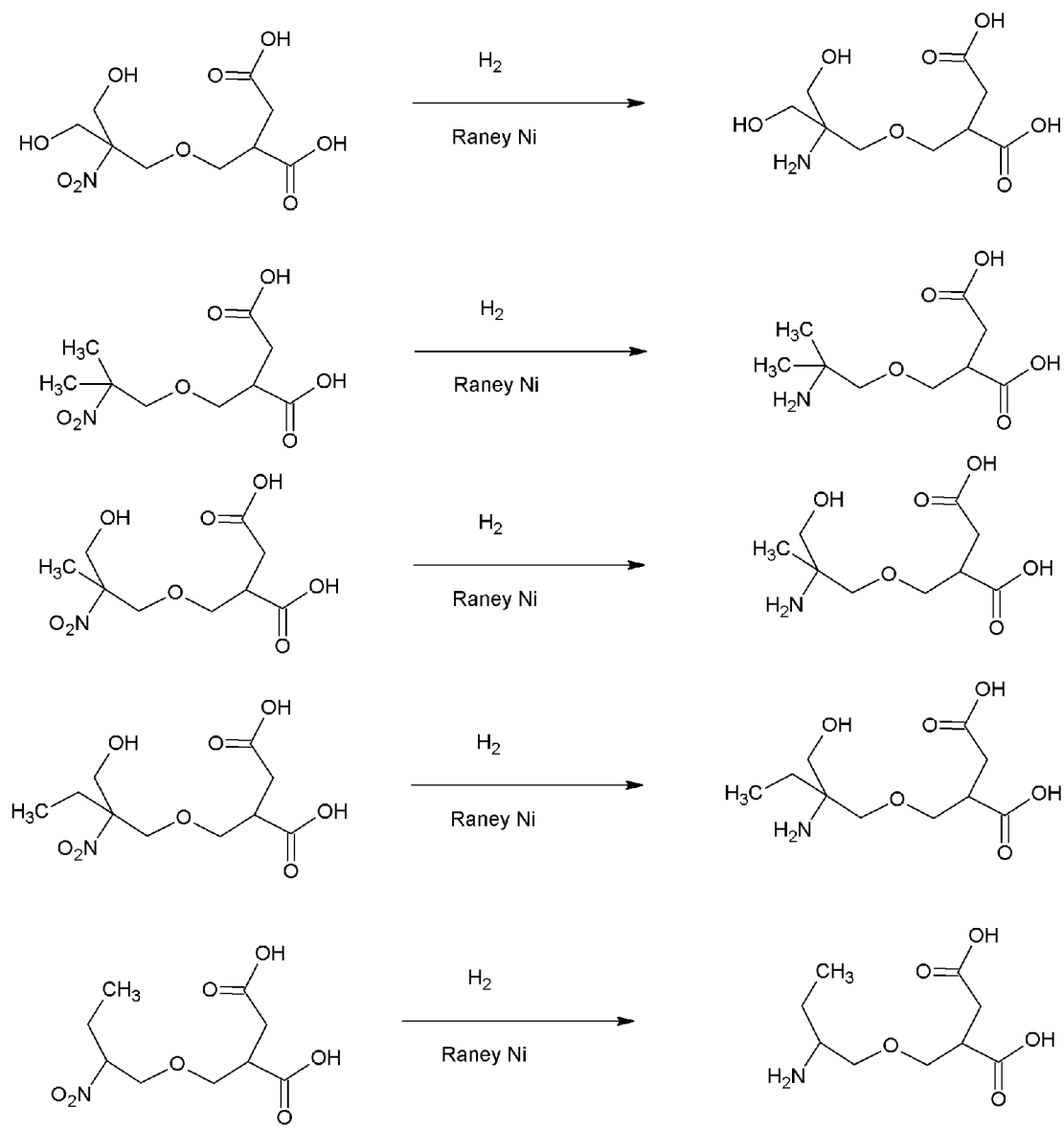
FIG. 44 shows the synthesis of primary amino zwitterionic buffers from nitro acids.

FIG. 42 teaches the synthesis of zwitterionic biological buffers from amino alcohols and itaconic acid. These buffers have two acid groups and increased buffering in the acidic range of pH 3-6. FIGS. 43 and 44 show the synthesis of zwitterionic buffers with primary amine groups. These buffers are preferred in applications such as personal care where secondary amines are seen as undesirable. The nitro diacids of FIG. 44 also have great utility as chemical intermediates when synthesizing bioactive molecules.

Figure 45:
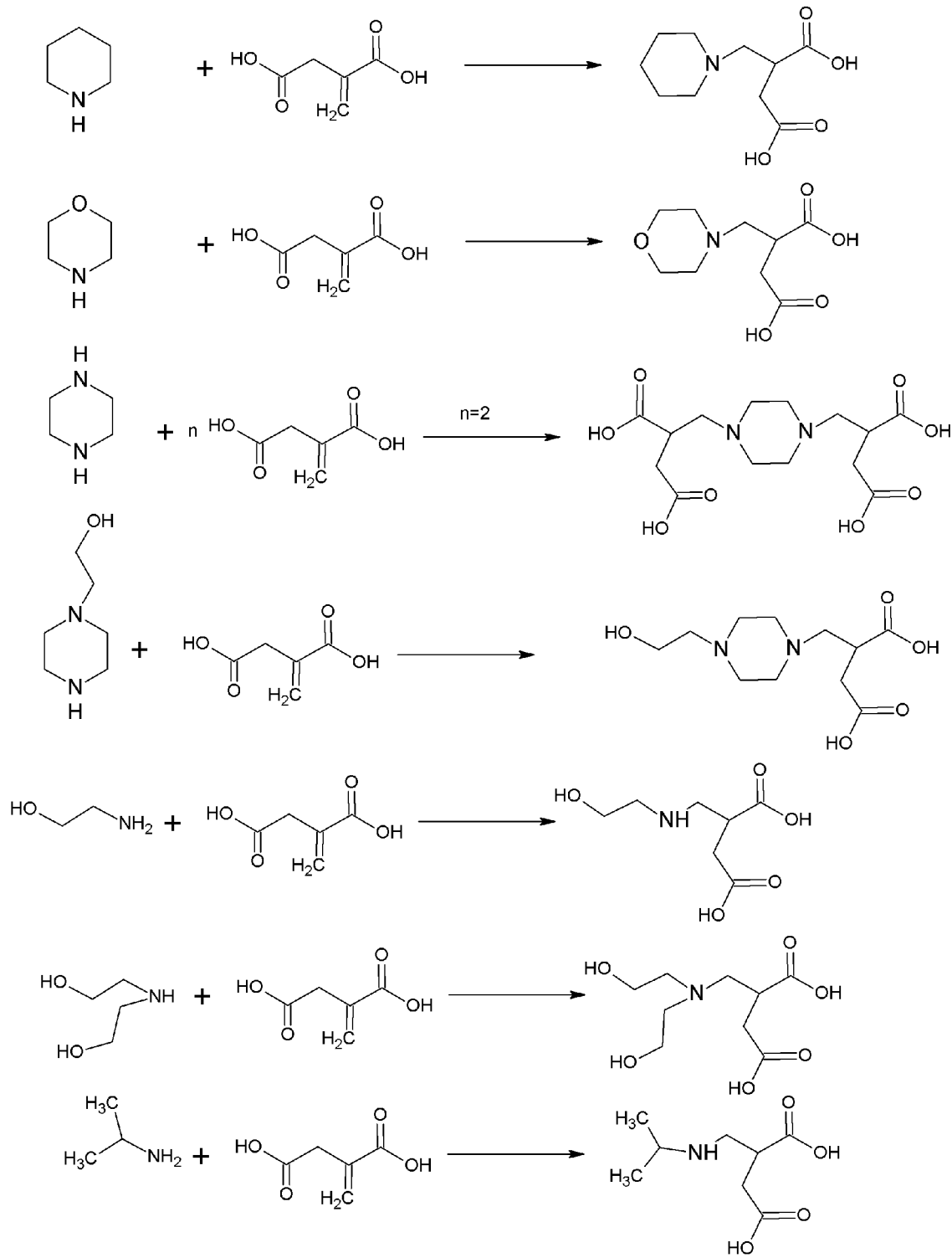
FIG. 45 shows the synthesis of a family of zwitterionic buffers from itaconic acid and amines.

FIG. 45 teaches the synthesis of a family of zwitterionic buffers from itaconic acid. The buffers in FIG. 45 are not limited to amino alcohols as starting materials and provide a wide range of molecular size and solubilities.

Figure 46:
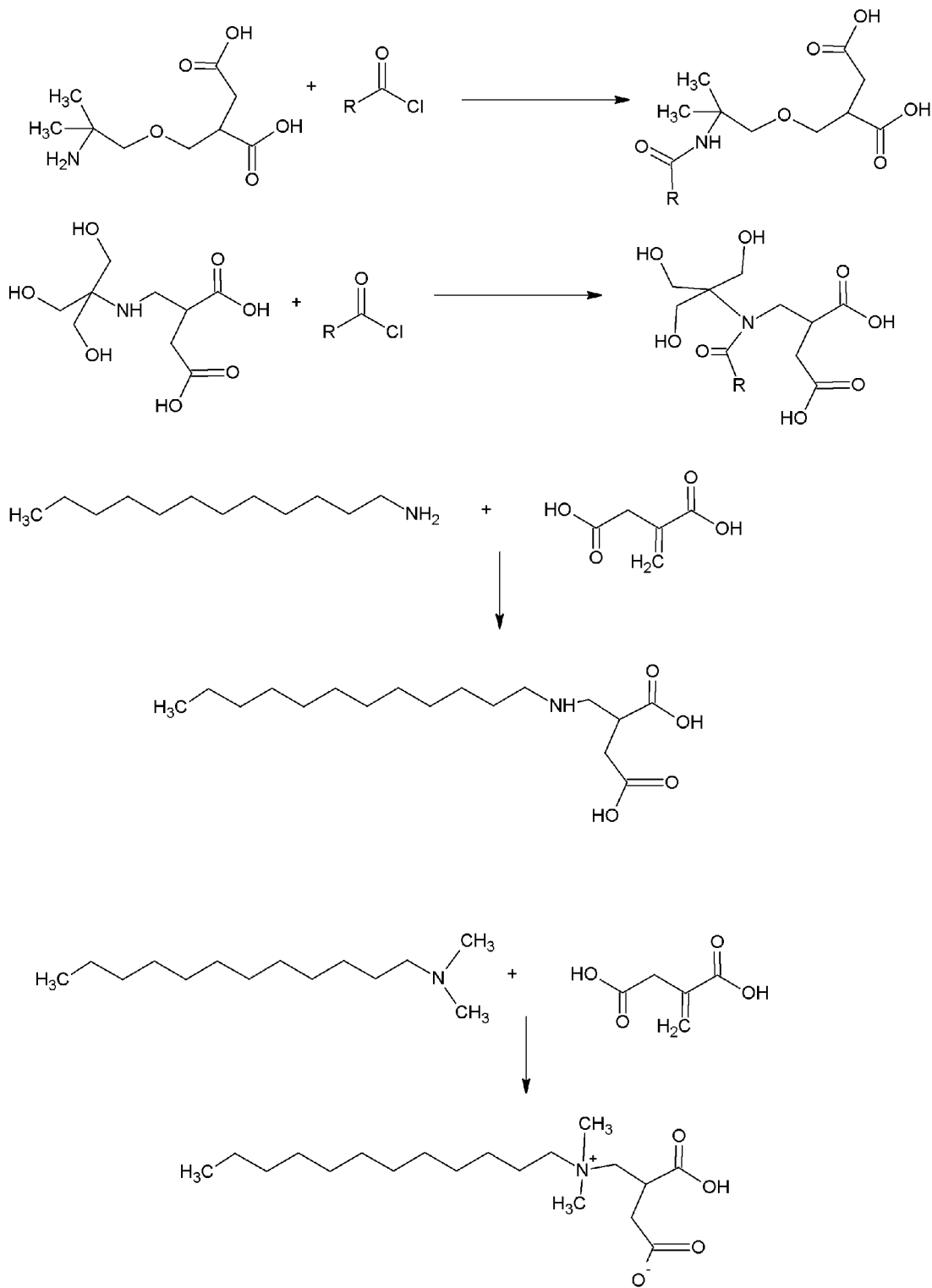
FIG. 46 shows the synthesis of surfactants from amines and itaconic acid intermediates.

FIG. 46 teaches the synthesis of a family of amphoteric surfactants. These surfactants are preferred for there mildness, ability to perform in hard water conditions and persistent lather when in the fatty tail is approximately 10-12 carbons in length. The R group in FIG. 46 is to encompass the fatty acid family of carbon chain lengths, generally from about 6 to about 22 carbons. In the specific cases illustrated of lauric amine and lauric dimethyl amine reacted with itaconic acid, it is understood by one in the art that any chain length amine can be used and is in within the scope of the invention herein. Particularly, but not limited to the fatty amines (carbon lengths of about 6 to about 22 carbons, branched and linear, saturated and unsaturated), isopropyl amine and butyl amine. The lower carbon chain lengths produce low foaming hard surface cleaners, while the carbon chains of about 8 to 10 tend to produce the most foam. Higher chain lengths find utility as mineral collectors in floatation processes such as those employed in iron and potash mining.

Figure 47:
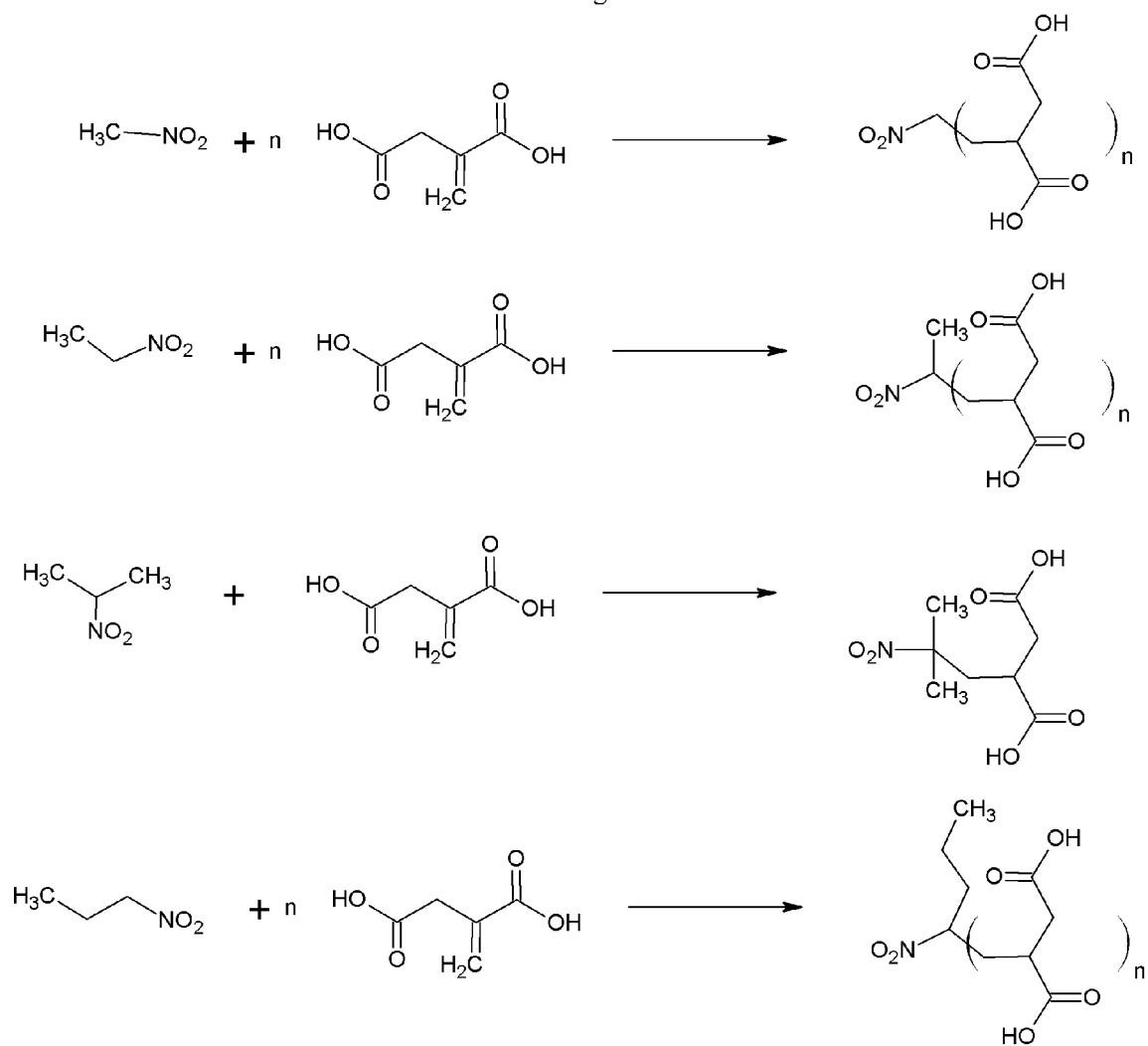
FIG. 47 shows the synthesis of nitroacids from nitroparaffins and itaconic acid.
Figure 48:
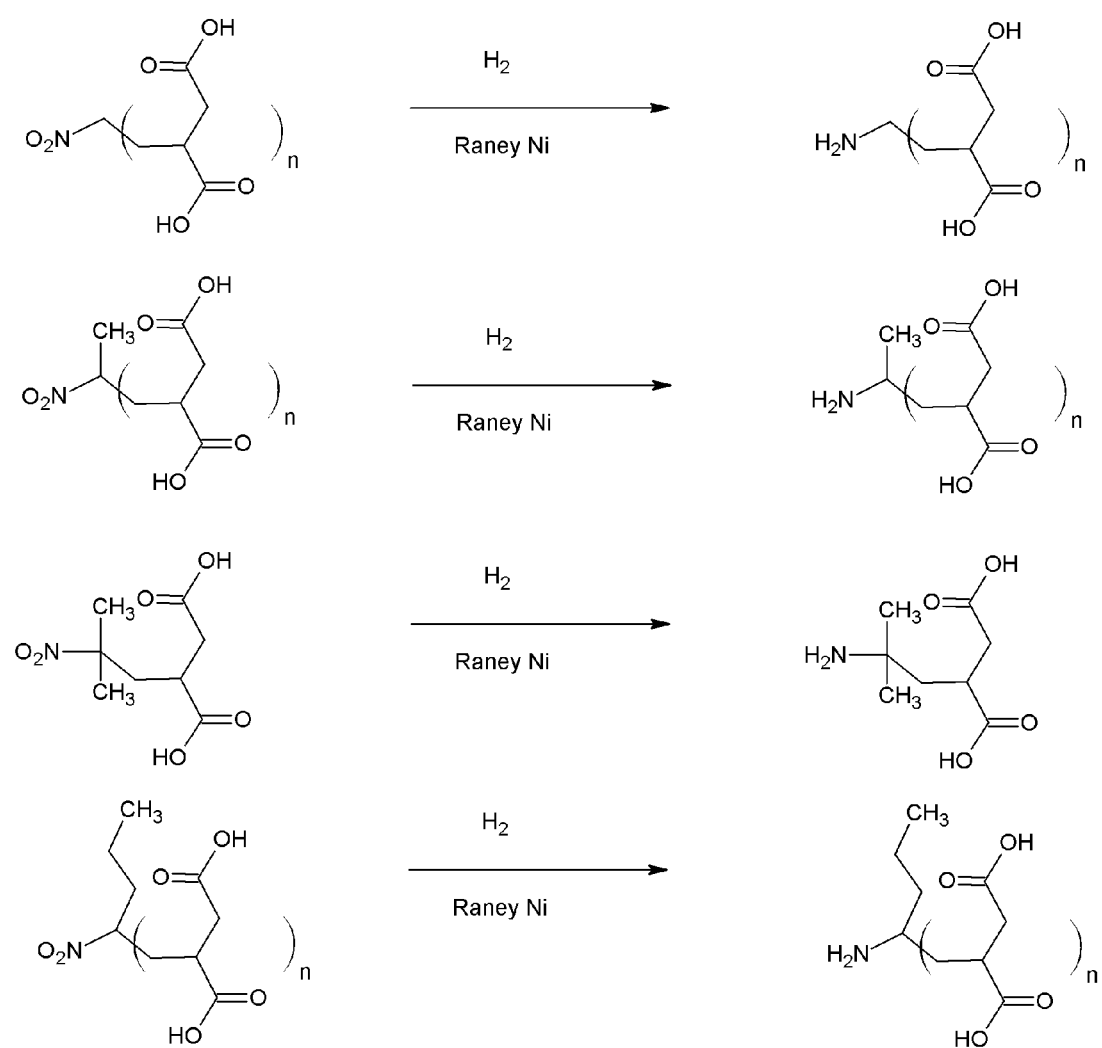
FIG. 48 shows the synthesis of zwitterionic buffers from nitro acids.

FIG. 47 shows the synthesis of nitro acids from nitroparaffins. As stated early, these are very flexible intermediates, particularly when synthesizing bioactive molecules. Reduction of the nitro acids, as shown in FIG. 48 produces zwitterionic buffers with primary amine character. In the case of nitroparaffins that have more than one hydrogen bound to the nitro bound carbon, more than one addition of the itaconic acid can occur. The substitution can occur up to the number of hydrogen atoms bound to the nitro bound carbon.

As outlined earlier, it is obvious to one skilled in the art that the resulting amines can be reacted further with vinyl acids, monochloroacetic acid, sodium vinyl sulfonate, or an oxirane sulfonate to further add acidic character to the zwitterionic buffer.

Several descriptions and illustrations have been presented to enhance understanding of the present invention. One skilled in the art will know that numerous changes and variations are possible without departing from the spirit of the invention. Each of these changes and variations are within the scope of the present invention.

I claim:

1. A biological buffer of the following structure:

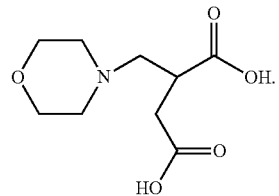

2. A surfactant of the following structure:

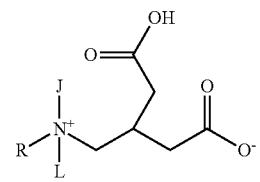

where R is a linear or branched, saturated or unsaturated hydrocarbon of from 6 to 22 carbons, and J and L are independently chosen from —$CH_3$ or —$CH_2CH_3$.

3. The surfactant of claim 2 where R=—$C_{12}H_{25}$ and J=L=—$CH_3$.

4. A biological buffer of the following structure:

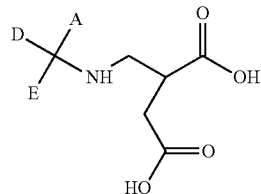

Wherein A, D, and E are the same or different and are independently chosen from the group containing: —$CH_2OH$, —$CH_3$, —$CH_2CH_3$.

5. A biological buffer of the following structure:

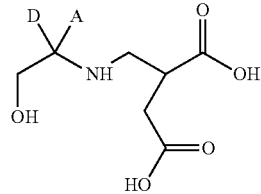

Wherein A and D are the same or different and are independently chosen from the group containing: —H, —$CH_2OH$, —$CH_3$, —$CH_2CH_3$.

6. The biological Buffer of claim 4 where A, D, and E are all —$CH_2OH$.

7. The biological buffer of claim 4 where A and D are —$CH_3$ and E is —$CH_2OH$.

* * * * *